(12) United States Patent
Welker

(10) Patent No.: US 8,350,228 B2
(45) Date of Patent: Jan. 8, 2013

(54) GERMICIDAL FIXTURE AND METHODS

(75) Inventor: Mark L. Welker, Houston, TX (US)

(73) Assignee: Arcalux Corporation, Houston, TX (US)

( * ) Notice: Subject to any disclaimer, the term of this patent is extended or adjusted under 35 U.S.C. 154(b) by 120 days.

(21) Appl. No.: 12/800,685

(22) Filed: May 20, 2010

(65) Prior Publication Data

US 2011/0001060 A1    Jan. 6, 2011

(51) Int. Cl.
*A61L 9/20* (2006.01)
(52) U.S. Cl. ............... 250/455.11; 250/504 R; 250/435
(58) Field of Classification Search .......... 250/435–438, 250/455.11
See application file for complete search history.

(56) References Cited

U.S. PATENT DOCUMENTS

| | | | |
|---|---|---|---|
| 2,398,627 A * | 4/1946 | Disbro et al. ................ 454/68 |
| 3,078,366 A | 2/1963 | Winkler | |
| 3,087,981 A | 4/1963 | Harling | |
| 4,188,656 A | 2/1980 | Howard | |
| 4,455,594 A | 6/1984 | Yang | |
| 4,691,267 A | 9/1987 | Giesberg | |
| 4,967,324 A | 10/1990 | Barclay | |
| 5,128,850 A | 7/1992 | Juodvalkis | |
| 5,997,812 A * | 12/1999 | Burnham et al. ............... 422/24 |
| 6,010,230 A | 1/2000 | Schmidt et al. | |
| 6,059,424 A | 5/2000 | Kotloff | |
| 6,854,860 B2 | 2/2005 | Plunk | |
| 2002/0031460 A1 | 3/2002 | Kulp | |
| 2003/0146082 A1* | 8/2003 | Gibson et al. ............. 204/157.3 |
| 2003/0155228 A1 | 8/2003 | Mills et al. | |
| 2004/0213003 A1 | 10/2004 | Lauderdale et al. | |
| 2006/0057020 A1* | 3/2006 | Tufo ............................ 422/24 |
| 2006/0152921 A1 | 7/2006 | Welker | |
| 2007/0181000 A1 | 8/2007 | Wilson et al. | |
| 2007/0253205 A1 | 11/2007 | Welker | |
| 2009/0004046 A1* | 1/2009 | McEllen ........................ 422/2 |
| 2010/0044319 A1* | 2/2010 | Engel et al. .................. 210/746 |
| 2010/0090840 A1* | 4/2010 | Schreiner ..................... 340/600 |

* cited by examiner

*Primary Examiner* — Jack Berman
*Assistant Examiner* — Eliza Osenbaugh-Stewart
(74) *Attorney, Agent, or Firm* — The Matthews Firm

(57) ABSTRACT

The present disclosure relates to adapting a commonly used lighting fixture that is generally specified as the primary lighting source for illuminating a particular area as the apparatus for enclosing an additional UV lighting mechanism. Further, the disclosure relates to a device that can be integrated into a light fixture used with a suspended grid ceiling or a solid ceiling. Also, the present disclosure relates to a germicidal fixture used in association with a light fixture, and to an apparatus for a new germicidal light fixture and for replacing or converting an existing light fixture for efficient germicidal use.

12 Claims, 29 Drawing Sheets

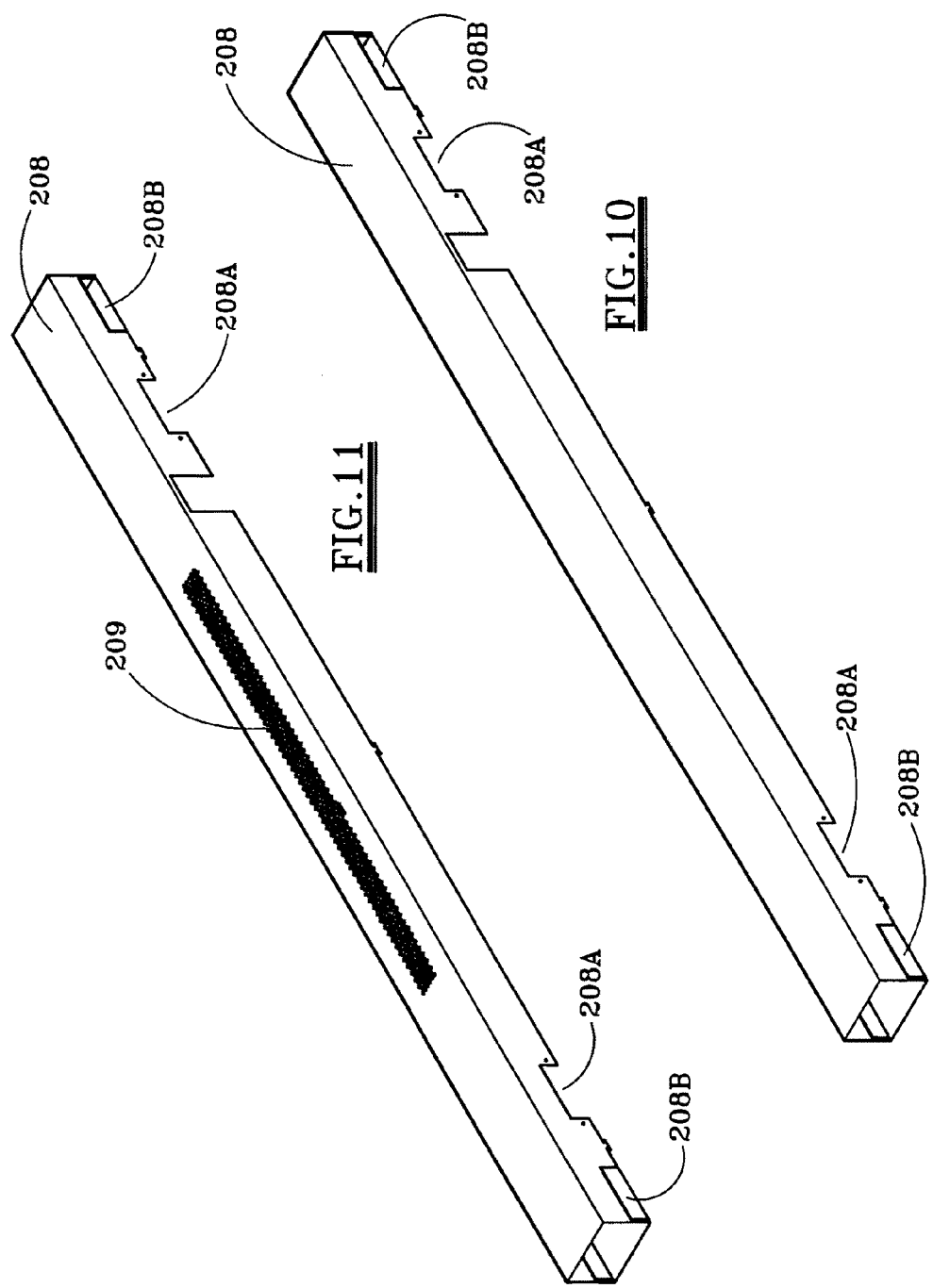

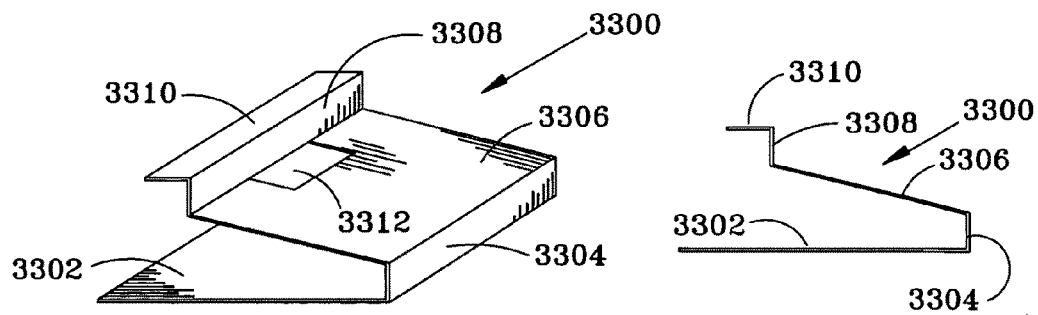
FIG.33A
FIG.33B
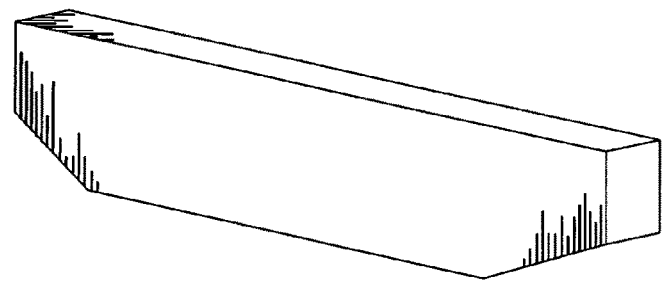
FIG.34
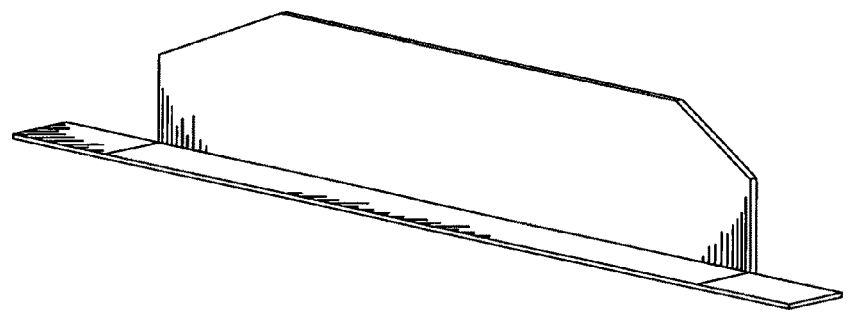
FIG.35

GERMICIDAL FIXTURE AND METHODS

FIELD OF THE INVENTION

The present disclosure relates generally to the field of "Germicidal Eradication" for certain airborne microorganism through the use of "Ultraviolet Light," generically refereed to as UV lighting. More particularly, the present disclosure relates to adapting a commonly used lighting fixture that is generally specified as the primary lighting source for illuminating a particular area as the apparatus for enclosing the additional UV lighting mechanism. Further, the disclosure relates to a device that can be integrated into a light fixture used with a suspended grid ceiling or a solid ceiling. Also, the present disclosure relates to a germicidal fixture used in association with a light fixture, and to an apparatus for a new germicidal light fixture and for replacing or converting an existing light fixture for efficient germicidal use.

BACKGROUND OF THE INVENTION

Typically in facilities with high traffic of human presence is where the possibility of airborne germs are most likely to be present and the need to reduce the percentage of transmitted airborne microorganisms associated to infectious disease is desired. The effect to humans of such transmitted disease as it relates to immediate sickness from direct exposure or to the delayed effects associated to secondary infections are well documented. The industry acceptance for reducing these airborne germs and microorganisms is widely desired and sought after. Also, it is appreciated that the use of Ultraviolet Light or UV light over other methods such as chemicals is widely appreciated.

The use of UV light in water treatment for fortifying potable water and for its use in Heating Ventilating Air Conditioning ("HVAC") systems for reducing mold and containment build up on coils has a proven and successful track record. The ability of UV light to kill bacteria on surfaces of general use equipment such as hair clippers and other utensils, as used in beauty salons, can be observed in use on a daily bases.

The most common practice for eradicating microorganisms in areas such as hospital rooms is usually related to microorganisms that are transmitted through direct contact with an object, not airborne. The methods currently in practice for controlling surface related bacteria are associated to chemical wipes, or disinfectant sprays and other various contact methods. All of these methods require direct contact with the microorganisms, and some for prolonged periods of time, to effectively eradicate the bacteria. In most cases, a large percentage of microorganisms present are not killed. The microorganisms are not killed for many reasons, such as for example, because the chemical evaporates to quickly, allowing the microorganism to either mutate or build an immunity to the chemical thus becoming more dangerous and harder to eradicate in the future because of its mutation capabilities. None of these methods addresses the eradication of airborne microorganism.

Whereas, the advantage of UV light which has a higher percentage of effectiveness for eradication and does so with the capability of eliminating the bacteria's capacity to mutate and become more dangerous and problematic to eradicate in the future. The current UV lighting devices only kill the airborne microorganisms that come in site of the light. This UV technology is static in design, it can be seen in other industries such as food preparation areas and restaurant dinning rooms, but their effectiveness still relies on the volume of air that passes within its line of site. Because of the danger of ultraviolet exposure to the skin and eyes, the placement of lamp technology within these designs is not usually conducive with treatment for high volumes of air, thus limiting their effectiveness to treat large volume areas effectively.

Therefore, the use of an "Ultraviolet Light" system capable of eradicating "airborne" bacteria designed as either a retrofit kit or a stand-alone design to be coupled into the body of a light fixture designed for use in a suspended grid ceiling or a solid ceiling applications would be both desirable and practical.

Typically in buildings, suspended ceilings having a metallic grid that supports panels in grid openings are common. Generally, in such ceilings, direct lighting fixtures replace panels in selected grid openings to provide room illumination. Such light fixtures are usually open bottom boxes that have a number of fluorescent lamps mounted in the box, in parallel, with a translucent or parabolic cover on the bottom of the box. The box is supported on the grid. In direct lighting, light from the lamps shines directly downward through a translucent or parabolic cover into the room. Generally, the lamps are visible from below. Such direct form of fluorescent lighting is relatively inexpensive, but very plain and utilitarian, without much decorative effect or the ability to upgrade to future lamp technologies of various lengths or quantities and without consideration for simplifying the related maintenance issues associated with the normal operations of a florescent lighting fixture.

Also an indirect or reflected type of fluorescent lighting is used with suspended grid ceilings as well as fixed ceilings. In such indirect lighting, the fluorescent lamps are less visible or cannot be seen, but the lighting yields a glow over the room, which can be used to achieve desirable decorative effects. Translucent to opaque covers, panes or lenses are normally used with this type of lighting. The light shines through open space into the room after being reflected. In one form of indirect lighting, the lamps are positioned below the ceiling panels of the suspended ceiling, and reflect against the ceiling into the room. An opaque shield conceals viewing the lamps from the room below. Such installations are generally custom designed and installed, with attendant, generally extensive, expense.

To avoid the expense of custom designing and installing indirect lighting which reflects against the ceiling, indirect lighting fixtures can be supported in grid openings as in direct lighting fixtures. In this form of indirect lighting in suspended grid ceilings, the fixture reflects light through a grid opening itself, as in U.S. Pat. No. 5,709,460. In the referenced patent, the lamps are positioned above and behind panels adjacent the openings. The lamps are concealed from view. The light is reflected from a dome over the opening and lamps, into the room below, through the grid opening. A mask or trim is optionally secured to the fixture to reduce the area of the opening through which the reflected light travels, and to further conceal the lamps from view from below. The fixture, including the reflector dome, rests on the grid beam flanges.

The light produced by a fluorescent lamp is generated by an electric current being conducted through mercury and inert gases. Fluorescent lighting is generally used, but not always, in indoor applications for both ambient and task lighting. The most commonly used types of fluorescent lamps are 2 foot by 2 foot (2'×2'), 2 foot by 4 foot (2'×4') and 1 foot by 4 foot (1'×4') lamps, and others exist of different dimensions, but the others are not as common when associated with applications for ambient or task lighting indoors. Fluorescent fixtures and lamps are preferred for ambient and task lighting in large areas because their visual efficiency creates less direct glare than do incandescent bulbs, and because fluorescent lighting is several times as energy efficient as incandescent lighting.

Although fluorescent lamps are generally energy efficient, there are more efficient lamps that use improved electrodes and coatings when compared to older fluorescent lamp types. These lamps produce increased lumen output with improved and substantially lower power consumption. The current lamps can be replaced with energy-saving lamps of lesser wattage and improved visual aspects, but the current fixtures are currently restricted by the necessity of having to use the same length and configuration of lamps as originally designed by the manufacturer, even when lamps of shorter lengths exist and the shorter lamps would allow an even greater improvement in energy savings or more practical to an application task. Also, more energy efficient ballasts are available. These improved ballasts can measurably increase the energy efficiency of the fixture.

A large market exists for new light fixtures as well as for the upgrading of existing fluorescent lighting in any appropriate applications, including but not limited to office buildings, residential buildings, warehouses, retail centers, hospitals, airports, schools, colleges, municipal buildings and factories, to install modern energy efficient lamps and ballasts. In addition, many older fluorescent light fixtures were installed because at that time they were the most efficient. With today's concern for energy efficiency and cost reduction, it is desirable to upgrade a current fluorescent fixture to one having a more energy efficient design related to the application task. When upgrading a fixture, it is important to use a fixture that is flexible and expandable to provide options for future lamp trends and standards. As used herein, expandability refers to the length of the lamps and the flexibility refers to the number of lamps in each fixture.

Often times, a single building will have a plurality of fixture sizes. At present, a separate different light fixture is required for each fixture configuration holding one or more fluorescent lamps. In a given structure, this may vary from one or two different fixture configurations to a multiple number of configurations, but is typically not restricted. Manufacturers must therefore make and stock a commensurate number of individual, different fixture configurations for fluorescent lamps.

There exists, therefore, a need for a fixture apparatus having enhanced expandability and flexibility with respect to existing structures and the fixtures therein.

It would therefore be useful to provide a light fixture that can hold a multiple number of lamp configurations of various fluorescent lamp lengths and lamp types, and the fixture is interchangeable via kit(s) or specifically designed to incorporate the configuration of ultraviolet lighting for the purpose of germicidal eradication of certain airborne microorganism.

A feature of the present disclosure is to provide a mechanical device that can pull large volumes air into a cleansing chamber containing ultraviolet lighting.

Another feature of the present disclosure is to wash the air of the harmful contaminates before it is returned back into to the same area through the use of germicidal ultraviolet lighting.

Yet another feature of the present disclosure is to have the ability to incorporate the use of multiple UV lamp technologies such as LED, fluorescent, excimer, incandescent and others, without limitation.

Yet another feature of the present disclosure is to totally encapsulate the UV lamps eliminating the possibility of light exposure to harmful UV rays during normal operation and periodical maintenance issues.

Yet another feature of the present disclosure is to be contained in tandem within a common light fixture that can be placed safely in areas and used as general lighting in highly populated areas by the general public.

Yet another feature of the present disclosure is the capability to monitor itself for maximum effectiveness of germicidal eradication, coupled with warning sensors capable of notifying the proper entities the need for maintenance.

Yet another feature of the present disclosure is the capability of automatically turning off power to UV Lamps and mechanical air movement devices once the area containing the UV apparatus within the fixture housing is opened for any reason.

Yet another feature of the present disclosure is designed for all parts to be handled and maintained with the use of general labor without the need of tools or specialty training for replacement of parts.

Yet another feature of the present disclosure is the ability to supply kits that are various in design and scope that are able to achieve different configurations of lamps and motor controls, and have various aesthetic concepts for numerous markets.

Yet another feature of the present disclosure is to supply these kits with plug and play capability for ease of replacement or addition of technologies as a kit to the existing fixture.

It would therefore be useful to provide a single light fixture that can hold a multiple number of lamp configurations of various fluorescent lamp lengths and lamp types, and thus the fixture is interchangeable.

A feature of the present disclosure is to provide a light fixture system with the capacity to be converted from a direct lighting fixture to an indirect lighting fixture and capable of providing the various aesthetic, maintenance, and improved efficiencies and options as requested or required to improve or meet desired task lighting.

A feature of the present disclosure is to provide a light fixture system having a fixture housing equipped with various removable perforated slots allowing the fixture the ability to use various lamp lengths, lamp types and lamp configurations without having to purchase or use a new fixture housing.

A feature of the present disclosure is to provide a light fixture system having all the necessary parts being removable and re-configurable in the field or at manufacturing facility to accommodate various lamp configurations reducing the need for an electrician or other skilled technician, or only requiring a non-skilled technician as allowed by the relevant laws or ordnances.

Another feature of the present disclosure is to provide a light fixture system having all the necessary parts being removable and re-configurable in the field or at manufacturing facility to accommodate various lamp types, lengths, wattage, sizes and parts while reducing the need for an electrician or other skilled technician as allowed by the relevant laws or ordnances.

Yet another feature of the present disclosure is to provide a light fixture system having all the necessary parts being removable and re-configurable in the field or manufacturing facility to accommodate various lamp quantities reducing the need for an electrician or other skilled technician as allowed by the relevant laws or ordnances.

Another feature of the present disclosure is to provide a light fixture system that can be easily reconfigured without disengaging the fixture from the ceiling or, in many cases from, its power source.

Yet another feature of the present disclosure is to provide a light fixture system that can be easily serviced without disengaging the fixture from the ceiling or, in many situations from, its power source and typically without the need for an electrician, skilled laborer or other qualified technician as allowed by the relevant laws or ordnances.

Another feature of the present disclosure is to provide a light fixture system such that the fixture is easily accessed for replacement of electronic parts or other possible maintenance considerations without the need of specialty tools or an electrician, skilled laborer or other qualified technician as allowed by the relevant laws or ordnances.

Another feature of the present disclosure is to provide a light fixture system that provides for the installation of the fixture of the present disclosure without the removal of the existing fixture housing.

A feature of the present disclosure is to provide a light fixture system that has Shadow Box™ that is functional with respect to providing proportionality between the fixture configuration and the lamp characteristics of type and length.

Another feature of the present disclosure is to provide a light fixture system that has trim that is decorative.

Yet another feature of the present disclosure is to provide a light fixture system that has trim, which trim can be made of various materials, colors, textures, cuts, logos and designs.

Yet another feature of the present disclosure is to provide a light fixture system that has trim, which trim can be functional for illuminating a logo, image or slogan for advertising, branding or personalizing the fixture and the like.

Another feature of the present disclosure is to provide a light fixture system that has trim, which trim can be removed and replaced without the use of tools, special equipment or a qualified technician.

Another feature of the present disclosure is to provide a light fixture system that has trim, which trim is illuminated by light from the lamps in the fixture or from an auxiliary light source associated with the fixture.

Another feature of the present disclosure is to provide a light fixture system that provides lamp holders for various lamp configurations for several different types of lamps with no restriction as to the length of the lamp.

Another feature of the present disclosure is to provide a light fixture system for converting a fixture to a different configuration.

Yet another feature of the present disclosure is to provide a light fixture system that has trim, which trim is designed for the functionality of maximizing the performance parameters of the fixture in regards to but not limited to shorter lamp lengths, lamp positioning, lamp quantities, lens attachment, and other related features necessary to perform a preferred lighting task such as by way of example indirect lighting.

Yet another feature of the present disclosure is to provide a light fixture system that has trim, in regards to but not limited to, advertising a logo, image or slogan, or illuminating or projecting an image for the purpose of personalizing the fixture to custom specifications.

Yet another feature of the present disclosure is to provide a light fixture system that has trim for advertising, illuminating or projecting an image for the purpose of personalizing the fixture to custom specifications that uses the lamps incorporated in the fixture specifications designed for the task.

Yet another feature of the present disclosure is to provide a light fixture system that has trim for advertising, illuminating or projecting an image for the purpose of personalizing the fixture to custom specifications that uses an alternate illumination source for the purpose of illuminating or projecting the image, where such alternate illumination sources are, without limitation, LED lighting, cold cathode devices, CFLs, fluorescent, and the like.

Yet another feature of the disclosure is to provide a light fixture system where the ballast is mounted to the outside of the fixture so as to be away from the lamps and the associated heat generated thereby for providing a cooler running temperature for the ballast and lamps so as to optimize energy use, ballast life and lamp life.

Another feature of the present disclosure is to provide a light fixture system that can use various ballast lengths as deemed necessary by the lamp and power requirements.

Yet another feature of the present disclosure is to provide a light fixture system wherein the ballast can be changed without the need of tools, special equipment or a skilled technician, i.e., plug and play characteristics.

Yet another feature of the present disclosure is to provide a light fixture system having a ballast that is mounted on the outside of the fixture which ballast is easily accessed for replacement or maintenance.

Another feature of the present disclosure is to provide a light fixture system that provides a ballast cover that may be mounted on the back of the fixture which cover is perforated to allow excess heat to escape in models used in a non-insulated area of operation in which the ceiling insulation does not engage the ballast cover.

Yet another feature of the disclosure is to provide a light fixture system that provides a ballast cover with no openings for use when the fixture is used in an operation where ceiling insulation may contact the ballast cover or wiring surfaces of the fixture.

Yet another feature of the present disclosure is to provide a light fixture system having a ballast having a heat sink engaged therewith to optimize energy use, ballast life and lamp life.

Still another feature of the present disclosure is to provide a light fixture system adaptable for use with multiple ballasts as well as multiple ballast lengths and sizes.

Yet still another feature of the present disclosure is to provide a light fixture system having an install apparatus that engages the perimeter of an opening into which a fluorescent fixture will fit for removably accepting the fixture.

A feature of the present disclosure is to provide a light fixture system having an install apparatus upon which an old fixture rests such that a new fixture can be engaged to the install apparatus without removing the old fixture.

Another feature of the present disclosure is to provide a light fixture system having an install apparatus for accepting a fixture which fixture can be opened by pivoting or disengaging from the install apparatus.

Another feature of the present disclosure is to provide a light fixture system having an install apparatus for associating with the perimeter in which the install apparatus is engaged for providing an air return path.

Another feature of the present disclosure is to provide a light fixture system having an install apparatus for accepting a fixture which fixture can be disengaged and dropped for removal from the install apparatus with or without pivoting with respect to the install apparatus.

Yet still another feature of the present disclosure is to provide a light fixture system having an install extension apparatus that engages the perimeter of an opening into which a fluorescent fixture will fit for removably accepting the fixture and for lifting a low-profile fixture so that a deeper, new fixture can be used under the low-profile fixture.

Yet another feature of the present disclosure is to provide a light fixture that does not directly engage the ceiling, wall or T-grid into which it fits.

Yet another feature of the present disclosure is to provide a light fixture that is adapted for use with a surface mount box, which surface mount box accepts the install apparatus of the present disclosure.

Yet still another feature of the present disclosure is to provide a light fixture that has light guides for directing light through the opening of a trim member or any desired angle with respect to the Shadow Box™ trim.

Additional features and advantages of the disclosure will be set forth in part in the description which follows, and in part will become apparent from the description, or may be learned by practice of the disclosure. The features and advantages of the disclosure may be realized by means of the combinations and steps particularly pointed out in the appended claims.

SUMMARY

To achieve the foregoing objects, features, and advantages and in accordance with the purpose of the disclosure as embodied and broadly described herein, a germicidal kit and germicidal light fixture system and method is provided.

Modular Germicidal Insert

A modular germicidal insert is provided comprising an enclosure having a chamber, an ultraviolet (UV) light source, and an air mover. The modular germicidal insert is adapted to engage a light fixture. The chamber is adapted to provide mixing of the air passing through the chamber. The UV light source is provided at such a wavelength as to destroy bacterial matter, such as by way of example, disrupting the DNA process within the bacterial matter. A sensing device can be used to test the processed air to determine the appropriate germicidal effectiveness. An automatic cut-off can be used to control power consumption and prevent unwanted exposure. Thus, air is moved into the enclosure, circulated within the chamber, irradiated by the UV light source, sensed to determine adequate germicidal effectiveness, and released to the area adjacent to the enclosure.

Fixture Housing

The fixture housing is equipped with various removable perforated slots allowing the fixture the ability to use various lamp lengths, lamp types and lamp quantities without having to purchase or use a new housing. All the necessary/required parts, such as end plates and lamp holders, are removable and reconfigurable in the field or in the manufacturing facility to allow various lamp and other necessary light needs to be preformed. The housing is an apparatus that assembles without the use of specialty tools. In addition to providing light reflectivity, the additional functions of the housing apparatus is to provide the flexibility to configure the light fixture in any desired configuration with respect to the number of lamps, the length of lamps, the wattage of lamps and any other relevant parameter associated with the configuration of the light fixture. The modular germicidal insert is removably associated with the fixture housing.

In one embodiment of the present disclosure, the fixture rotates out of the T-grid with the ballast on the outside of the lamp cavity away from the heat associated with the lamps.

A method of assembly uses a plurality of the following: (1) housing, (2) end plates, (3) lock bar, (4) axles, (5) pins with springs, (6) electronics, (7) Shadow Box™ trim, (8) ballast cover, (9) tombstone covers, (10) lens cover, and (11) modular germicidal insert.

An embodiment of the present disclosure is to rotate out of the ceiling the fixture to (1) provide access to the electronics and the lamps, (2) install and remove the fixture, (3) provide easy maintenance, (4) easily move the entire fixture to another T-grid, and (5) install and maintain the modular germicidal insert.

A tombstone/lamp holder is provided. The tombstone/lamp holder is adaptable for use with various lamp configurations and for various different types of lamps (e.g., T8-T5), but is not restricted to any known lamp.

Ballast Configurations

The ability to use any ballast length and size as deemed necessary by the lamp and power requirements, and is not restricted to any particular ballast. The ballast can be changed without the need of tools, special equipment or hard wiring through the use of electrical connectors, and can be described as "plug and play."

The ballast is mounted on the outside of the fixture, but not limited to that location, which is easily accessed for replacement or maintenance, and can be described as "snap-in and snap-out." The ballast is mounted to the outside of the fixture away from the lamps and the heat generated which results in a cooler running temperature for the ballast to optimize energy use, ballast life and lamp life.

Ballast Cover

The ballast cover is mounted on the back of the fixture, but is not limited to that location, and may be perforated to allow excess heat to escape in models used in a non-insulated area of operation in which the ceiling insulation, if any, does not cover the ballast cover. An alternate ballast cover with no openings can be used when the fixture is used in an operation where ceiling insulation will contact the ballast cover or wiring surfaces of the fixture.

Install Apparatus

The install apparatus is to provide the removable engagement of the light fixture with any ceiling, wall, T-grid or the like.

The method in which the install apparatus is installed varies with the required situation. In one embodiment, the install apparatus can be installed by placing the individual pieces into the aperture associated with the ceiling, wall, T-grid or the like. Alternately, the install apparatus is easily assembled and then installed as a complete unit in the aperture associated with the ceiling, wall, T-grid or the like utilizing the interlocking panels.

The install apparatus allows the fixture to be easily accessed for replacement of electronic parts or other possible maintenance needs of the light fixture and the modular germicidal insert because the light fixture pivots from the install apparatus for providing easy access to the fixture and the modular germicidal insert. In one embodiment, the light fixture pivots from the channel lock groves of the install apparatus for providing easy access to the fixture and the modular germicidal insert.

Further, the install apparatus provides for the installation of the light fixture without the removal of the existing fixture, if desired.

The method of using an install apparatus with a light fixture for removeably affixing the light fixture in a ceiling/wall structure having an opening therein comprises (1) engaging the perimeter of the opening with the install apparatus, (2) engaging the light fixture with the install apparatus such that the light fixture is removeably engaged with respect to the ceiling/wall structure, (3) pivoting or disengaging the fixture from the install apparatus for providing easy access to all parts of the fixture for easy operation and maintenance of the fixture and (4) returning of the fixture to a mounted position during operation.

The method of using a install apparatus with a light fixture for removeably affixing the light fixture in a ceiling/wall structure having another existing light fixture in an opening therein, the method comprises (1) disengaging the existing light fixture from the opening in a direction away from the direction the existing fixture casts light, (2) engaging the perimeter of the opening with the install apparatus, and (3)

engaging the light fixture with the install apparatus such that the light fixture is removeably engaged with the install apparatus and the existing light fixture is resting on the light fixture which is thus removeably engaged with respect to the ceiling/wall structure.

Further, the fixture by itself can be used with its own "jack-up" kit device. This allows the fixture to be made deeper without changing or installing a "jack up kit" to the install apparatus.

The method of converting an existing light fixture for removeably affixing the light fixture in a ceiling/wall structure having an opening therein, the method comprises (1) removing the back of the fixture, (2) adapting a pivot/hinge/latch mechanism between the fixture and the removed back and (3) pivoting the back about the mechanism such that the back drops from the opening and can be accessed for maintenance. The pivoting back could also incorporate the use of tear out tabs for various lamp lengths.

The method of converting an existing light fixture for removeably affixing the light fixture in a ceiling/wall structure having an opening therein, the method comprises (1) using the housing of an existing fixture, (2) adapting a pivot/hinge/latch mechanism between the existing housing and a smaller fixture that fits into the housing and (3) pivoting the smaller fixture about the mechanism such that the smaller fixture pivots or drops from the housing of the existing fixture and can be accessed for maintenance. Alternately, the present disclosure provides a method of manufacturing a new light fixture for removeably affixing the light fixture in a ceiling/wall structure having an opening therein, the method comprises (1) using the housing of a fixture, (2) adapting a pivot/hinge/latch mechanism between the housing and a smaller fixture such that the smaller fixture fits into the housing and (3) pivoting the smaller fixture about the mechanism such that the smaller fixture pivots or drops from the housing and can be accessed for maintenance.

It can be appreciated by those skilled in the art that many configurations are possible and are not limited and many different configurations are available in practicing the present disclosure. Examples of configurations, without limitation, are: (1) install apparatus, (2) cover plate for ballast cover hole, optional, (3) ballast, optional, (4) lamps; (1) lamps, (2) ballast, (3) install apparatus, (4) wiring harness, optional; and (1) lamps, (2) ballast, (3) install apparatus, (4) wiring harness, optional, (5) plug & play connectors, optional, (6) blanks for ballast cover and lamp holders.

Shadow Box™ Trim

The Shadow Box™ trim can be removed and attached to the light fixture without tools or attachment mechanisms. One Shadow Box™ trim is easily interchanged with another Shadow Box™ trim. The Shadow Box™ trim provides decorative trim which can be made of various materials, colors, textures, designs and other characteristics. The Shadow Box™ trim can be manufactured with corporate logos or other branding or advertising designs and is not limited to corporate designs. For example, graphic designs, images of animals, equipment, directions, and the like can be adapted for use with the Shadow Box™ trim. The Shadow Box™ trim can be rotated and laid into place so as to be removed and replaced without being lifted above the T-grid.

The Shadow Box™ trim can also provide a means for an indirect lighting apparatus. Further, the Shadow Box™ trim can be used with a ceiling mount apparatus to place a light fixture on a solid ceiling or wall.

Thus, the Shadow Box™ trim can be of any color, texture, material or other characteristic. More particularly, but without limitation, the Shadow Box™ trim can be plain, bear a design, bear a picture of an animal, person, figure, or any other item, bear a logo, bear a particular branding, or convey advertising, all referred to simply as the design. The Shadow Box™ trim provides that the design therein can be illuminated. The illumination of the design in the Shadow Box™ trim can be provided by the lamps associated with the light fixture. Also, the design in the Shadow Box™ trim can be illuminated by an alternate light source. Examples of such alternate light sources are, without limitation, LEDs, lasers, cold cathode devices, CFLs and the like. The design in the Shadow Box™ trim can be displayed in different colors. The coloring of the design can be achieved by using colored mylar film, colored LEDs, prisms, or the like. The Shadow Box™ trim has quick release hinge tabs to easily pivot, remove and replace the trim.

Methods

One embodiment of the present disclosure is a method of installing a light fixture having a germicidal insert. The method of installing a light fixture as practiced by the present disclosuredisclosure into an aperture in a ceiling, wall or box where the aperture is defined by a perimeter comprises the steps of engaging an install apparatus with the perimeter of the aperture, engaging a fixture in a hanging relationship with the install apparatus, connecting a power source to the fixture, rotating the hanging fixture until the fixture is operational or functional with the perimeter of the aperture, securing the fixture in a flush or operational relationship with the perimeter of the aperture, and providing power to the fixture for lighting the fixture.

Another embodiment of the present disclosure is a method of changing a modular germicidal insert. The method of changing a modular germicidal insert in a light fixture as practiced by the present disclosuredisclosure wherein the light fixture is engaged in a pivotal relationship with an install apparatus comprising the steps of disengaging a latch mechanism between the fixture and the install apparatus which latch mechanism removably secures the fixture to the install apparatus, pivoting the fixture away from the install apparatus such that the modular germicidal insert is exposed and the fixture is hanging from a portion of the install apparatus, removing the old modular germicidal insert from the fixture, engaging a new modular germicidal insert on the fixture, pivoting the fixture for engagement with the install apparatus, and engaging the latch mechanism for securing the fixture to the install apparatus.

Another embodiment of the present disclosure is a method of changing a lamp in a light fixture. The method of changing a lamp in a light fixture as practiced by the present disclosure wherein the light fixture is engaged in a pivotal relationship by a trim member comprises the steps of disengaging a latch mechanism between the fixture and the trim member which latch mechanism removably secures the trim member to the fixture, pivoting the trim member away from the fixture such that the lamp in a cavity in the fixture is exposed and the trim member is hanging from a portion of the fixture, removing the old lamp from the cavity, and engaging a new lamp in the cavity of the fixture without displacing any other lamps or components, pivoting the trim member for securing the lamp in the cavity, and engaging the latch mechanism for securing the trim member to the fixture.

Yet another embodiment of the present disclosure is a method of changing a ballast. The method of changing a ballast in a light fixture as practiced by the present disclosure wherein the light fixture is engaged in a pivotal relationship with an install apparatus comprising the steps of disengaging a latch mechanism between the fixture and the install apparatus which latch mechanism removably secures the fixture to the install apparatus, pivoting the fixture away from the install apparatus such that the ballast cover is exposed and the fixture is hanging from a portion of the install apparatus, removing the ballast cover and the old ballast from the fixture, engaging a new ballast and the ballast cover on the fixture, pivoting the fixture for engagement with the install apparatus, and engaging the latch mechanism for securing the fixture to the install apparatus.

Yet still another embodiment of the present disclosure is a method of changing the location of a tombstone holder with respect to a fixture. The method of changing the location of a tombstone holder with respect to a fixture as practiced by the present disclosure comprises the steps of accessing the tombstone holder, releasing the tombstone holder from the fixture housing, relocating the tombstone holder to another location, securing the tombstone holder to the fixture housing at the new location.

Still another embodiment of the present disclosure is a method of using a Shadow Box™ trim or trim member with a light fixture. The method of using a Shadow Box™ trim or trim member with a light fixture as practiced by the present disclosure wherein the light fixture is engaged in a pivotal relationship by a trim member comprising the steps of disengaging a latch mechanism between the fixture and the trim member which latch mechanism removably secures the trim member to the fixture, pivoting the trim member away from the fixture such that the trim member is hanging from a portion of the fixture, removing the trim member from the fixture, engaging a new trim member with the fixture, pivoting the trim member for removably engaging the fixture, engaging the latch mechanism for securing the trim member to the fixture.

Yet another embodiment of the present disclosure is a method of installing an install apparatus in a T-grid. The method of installing an install apparatus in a T-grid as practiced by the present disclosure comprises the steps of engaging a first lateral member in congruence with a first lateral side of the T-grid, engaging a second lateral member in congruence with a second lateral side of the T-grid, engaging a first longitudinal member in congruence with a first longitudinal side of the T-grid, interlocking the first lateral member and the first longitudinal, interlocking the second lateral member and the first longitudinal, engaging a second longitudinal member in congruence with a second longitudinal side of the T-grid, interlocking the first lateral member and the second longitudinal member, interlocking the second lateral member and the second longitudinal member such that the lateral members and the longitudinal members define the install apparatus.

Another embodiment of the present disclosure is a method of changing the lamp configurations or the lamp quantities comprising the steps of accessing the tombstone holder, releasing the tombstone holder from the fixture housing, engaging a new tombstone holder with the desired number of tombstones, and securing the new tombstone holder to the fixture housing.

Yet another embodiment of the present disclosure is a method of using a light fixture extension as practiced by the present disclosure for placement into an aperture in a ceiling, wall or box where the aperture is defined by a perimeter comprises the steps of removing trim member from the fixture, disengaging the fixture from the install apparatus via a latch mechanism between the fixture and the install apparatus, removing the existing hardware, replacing the hardware onto an extension, attaching the extension to the fixture to the correct corresponding positions, adding an end extension to the end plates, replacing the fixture for engagement into the install apparatus via a latch mechanism between the fixture and the install apparatus, and replacing the trim member and locking into position.

Yet still another embodiment of the present disclosure is a method of using an install apparatus extension as practiced by the present disclosure for placement into an aperture in a ceiling, wall or box where the aperture is defined by a perimeter comprises the steps of removing the fixture from the install apparatus, removing the install apparatus from the opening and attaching extension elements to the install apparatus, replacing the install apparatus into the ceiling or wall cavity, and replacing the fixture and engaging into the install apparatus via a latch mechanism between the fixture and the install apparatus.

Still another embodiment of the present disclosure is a method of adapting a light fixture as practiced by the present disclosure for casting indirect light comprises the steps of removing the trim member, removing the lamps, lowering the fixture from the install apparatus, removing the electronics, adding the new electronics, rotating the fixture back into the install apparatus, securing the fixture into the install apparatus, installing the indirect reflective shield, adding the lamps, attaching the indirect apparatus to trim member, attaching the trim member to the fixture, and rotating the trim member into the fixture and securing it in place.

Yet still another embodiment of the present disclosure is a method of using an install apparatus with a light fixture as practiced by the present disclosure. The method of using an install apparatus with a light fixture as practiced by the present disclosure for placement into an aperture in a ceiling, wall or box where the aperture is defined by a perimeter comprises the steps of pushing the existing fixture up, engaging an install apparatus with the perimeter of the aperture, engaging a fixture in a pivotally hanging relationship with the install apparatus such that the existing fixture is resting above the fixture and the install apparatus, connecting a power source to the fixture, rotating the hanging fixture until the fixture is operational with the perimeter of the aperture, securing the fixture in a flush or operational relationship with the perimeter of the aperture, and providing power to the fixture for lighting the fixture.

Yet another feature of the present disclosure is to provide a light fixture system for providing indirect light having an installation apparatus that engages the perimeter of an opening into a trim member where an indirect lighting cover/mechanism can be attached without the aid of specialty tools or skilled labor for converting the direct lighting configuration into an indirect light configuration.

Yet still another feature of the present disclosure is to provide a light fixture system having an installation apparatus that converts the electrical components from a direct lighting system into an indirect lighting system without the aid of specialty tools or skilled labor.

Additional advantages and modification will readily occur to those skilled in the art. The disclosure in its broader aspects is therefore not limited to the specific details, representative apparatus, and the illustrative examples shown and described herein. Accordingly, the departures may be made from the details without departing from the spirit or scope of the disclosed general inventive concept.

BRIEF DESCRIPTION OF THE DRAWINGS

The accompanying drawings that are incorporated in and constitute a part of the specification illustrate preferred embodiments of the disclosure and together with the general description of the disclosure given above and the detailed description of the preferred embodiment given below, serve to explain the principles of the disclosure.

FIG. 10 is a perspective view of a preferred embodiment of ballast cover associated with the light fixture apparatus of the present disclosure.

FIG. 11 is a perspective view of a preferred embodiment of ballast cover associated with the light fixture apparatus of the present disclosure that provides for the venting of heat from the ballast cover.

FIG. 33A is a perspective view of a preferred embodiment of the lens clip of the present disclosure.

FIG. 33B is an elevation view of the preferred embodiment of the lens clip of the present disclosure as illustrated in FIG. 33A.

FIG. 34 is a perspective view of the preferred embodiment of a UV germicidal modular insert of the present disclosure.

FIG. 35 is a perspective view of another preferred embodiment of a UV germicidal modular insert of the present disclosure.

Additional advantages and modification will readily occur to those skilled in the art. The disclosure in its broader aspects is therefore not limited to the specific details, representative apparatus, and the illustrative examples shown and described herein.

Accordingly, the departures may be made from the details without departing from the spirit or scope of the disclosed general inventive concept.

DETAILED DESCRIPTION OF THE PREFERRED EMBODIMENTS

The above general description and the following detailed description are merely illustrative of the generic disclosure, and additional modes, advantages, and particulars of this disclosure will be readily suggested to those skilled in the art without departing from the spirit and scope of the disclosure.

Figure 1:
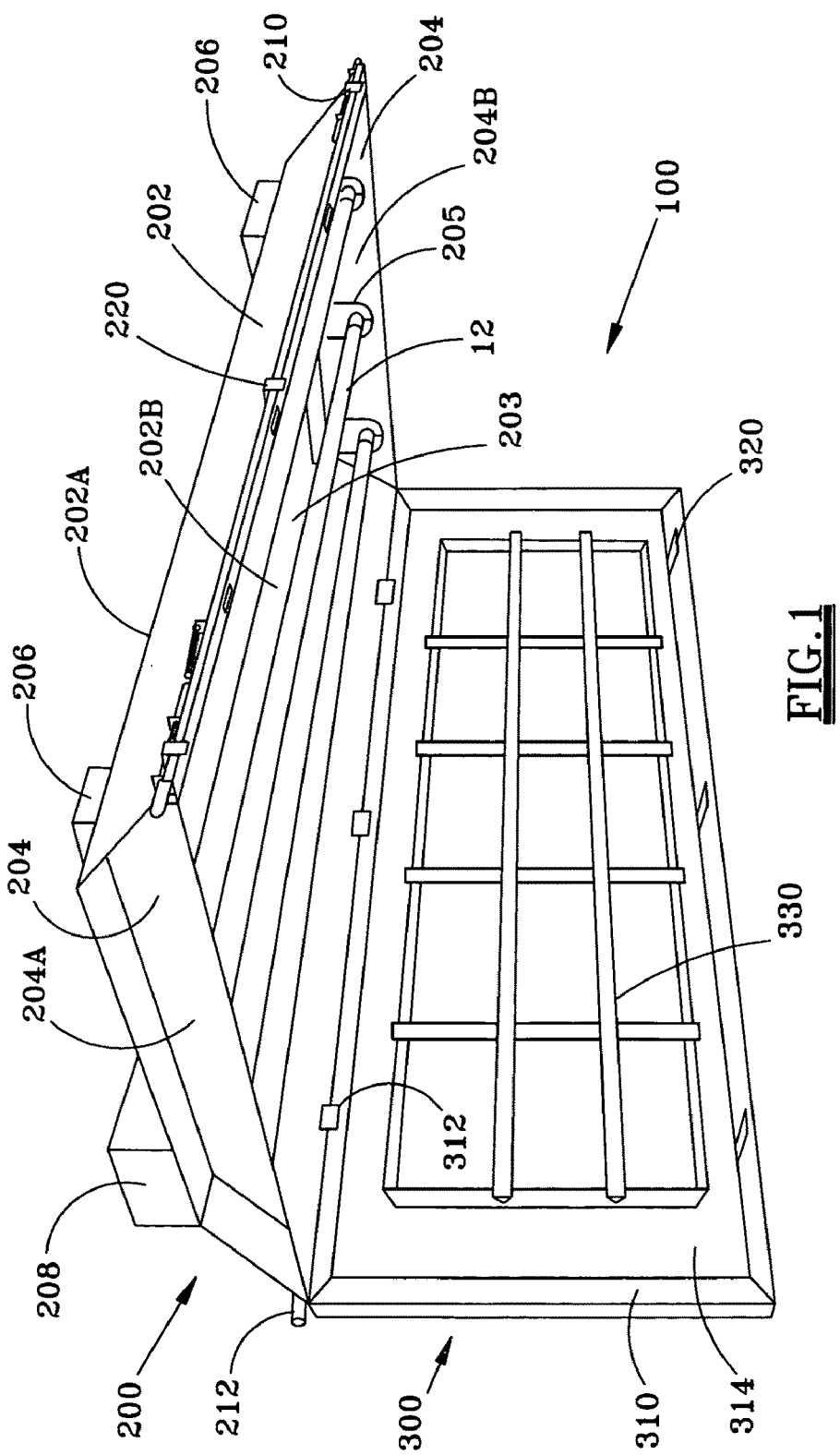
FIG. 1 is a perspective view of a preferred embodiment of the light fixture apparatus of the present disclosure with the Shadow Box™ trim pivoted from and disposed at a 90 degree angle to the fixture/troffer.

FIG. 1 is a perspective view of a preferred embodiment of the light fixture apparatus 100 of the present disclosure with the Shadow Box™ trim 300 pivoted from and disposed at a 90 degree angle to the fixture/troffer 200. The fixture/troffer 200 and the Shadow Box™ trim 300 have a detachable relationship as well as a pivoting relationship. Thus, the Shadow Box™ trim 300 can either be removed completely from the fixture/troffer 200, or the Shadow Box™ trim 300 can be in a pivoting relationship with the fixture/troffer 200.

The fixture/troffer 200 comprises a base 202, end plates 204, lamp holder covers 206, a ballast cover 208, a fixture release mechanism 210 and a pivot member 212 for the fixture/troffer 200. The base 202 has a convexed surface 202A and a concaved surface 202B. The end plates 204 have an outer surface 204A and an inner surface 204B. The concaved surface 202B of the base 202 and the inner surfaces 204B of the end plates 204 form a cavity 203. The cavity 203 accepts one or more lamps 12. The lamps are held in place by a plurality of lamp holders or tombstones 205.

The Shadow Box™ trim 300 comprises a perimeter structure 310, a pivot member 312, a display surface 314, an engaging mechanism 320 and a lens 330. The pivot member 312 of the Shadow Box™ trim 300 removeably engages the perimeter of the base 202 of the fixture/troffer 200 such that the Shadow Box™ trim 300 pivots about a perimeter of the fixture/troffer 200. In FIG. 1, the Shadow Box™ trim 300 is illustrated to be in an open-pivoted relationship with and disposed at a 90 degree angle to the fixture/troffer 200. It can be readily appreciated that the Shadow Box™ trim 300 can be moved about the pivot member 312 to be in a closed-pivoted relationship with the fixture/troffer 200. The Shadow Box™ trim 300 is held in a closed-pivoted relationship with the fixture/troffer 200 by the engaging mechanism 320 interacting with the release mechanism 220.

Figure 2:
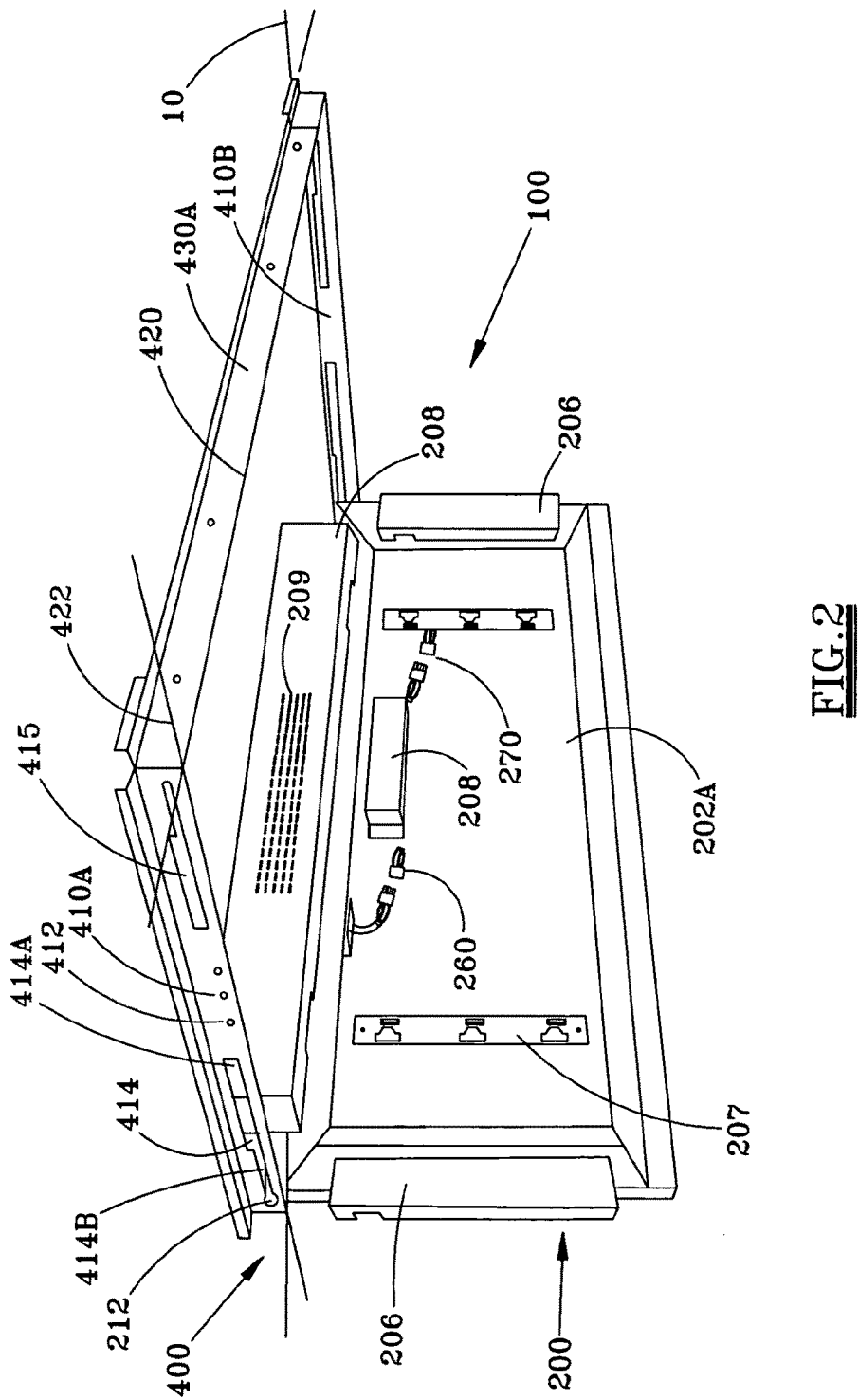
FIG. 2 is a perspective view of a preferred embodiment of the light fixture apparatus of the present disclosure with the fixture/troffer pivoted from and disposed at a 90 degree angle to the install apparatus which is engaged with a T grid.

FIG. 2 is a perspective view of a preferred embodiment of the light fixture apparatus 100 of the present disclosure with the fixture/troffer 200 pivoted from and disposed at a 90 degree angle to the install apparatus 400 which is engaged with a T grid 10. The fixture/troffer 200 and the install apparatus 400 have a detachable relationship as well as a pivoting relationship. Thus, the fixture/troffer 200 can either be removed completely from the install apparatus 400, or the fixture/troffer 200 can be in a pivoting relationship with the install apparatus 400.

The fixture/troffer 200 illustrated in FIG. 2 shows the concaved side 202A. The fixture/troffer 200 is illustrated with the lamp holder covers 206, the tombstone holders 207, the ballast 20, the power source-to-ballast connectors 260, the ballast-to-tombstone connectors 270, the convexed surface 202A of the base 202, the ballast cover 208 and the ventilation grid 209 in the ballast cover 208.

The install apparatus 400 is shown engaged with the T-grid 10. The install apparatus 400 includes the lateral members 410A, 410B and the longitudinal members 430A, 430B [latter not shown]. The longitudinal members 430A, 430B of the install apparatus 400 are illustrated engaging longitudinal portions of the T-grid 10. The longitudinal members 430A, 430B are preferably made of angled material such as for example U-shaped metal. Particularly, the longitudinal member 430A shown in FIG. 2 illustrates the concaved side thereof with a smaller side engaging the T-grid 10 and the other smaller side remote from the T-grid 10. The longitudinal members 430A, 430B may have one or more extensions from a remote end for removeably engaging the lateral members 410A, 410B, such as one or more extensions [not shown]. The extensions protruding from the longitudinal members 430A, 430B can be configured to be accepted in the respective lateral members 410A, 410B to form a detent [not shown] at an end location 422 for locking the movement of the lateral members 410A, 410B and the longitudinal members 430A, 430B. Also, the end remote from the detent may be secured to the T-grid 10 by use of a screw in the holes 412 illustrated in the lateral members 410A, 410B and the longitudinal members 430A, 430B or by any other conventional securing mechanism.

Of importance is the channel-lock feature of the fixture/troffer 200 relative to the install apparatus 400. The fixture/troffer 200 has the pivot member 212 extending from one side of its perimeter. The pivot member 212 has at both its extremities an expanded portion that has a larger radial dimension than the main portion of the pivot member 212. The install apparatus 400 has one or more slots 414 in each lateral member 410A, 410B. The slot 414 has a larger portion 414A and a smaller portion 414B. The larger portion 414A is for receiving there through the expanded portion of the pivot member 212. As the pivot member 212 is pushed from the larger portion 414A into the smaller portion 414B of the lateral member 410A, 410B, the pivot member 212 is secured in the smaller portion 414B of the lateral members 410A, 410B such that the expanded portion of the pivot member 212 is on one side of the lateral members 410A, 410B and the main portion of the pivot member 212 along with the fixture/troffer 200 are on the other side of the lateral members 410A, 410B such that the fixture/troffer 200 is encompassed by the pivot member 212. Also illustrated is alternate slot 415 which can be used in place of the slot 414. It can be appreciated by those skilled in the art that alternate means are or could be available to perform the same function as the channel-lock feature of the present disclosure and such alternate means are encompassed by the present disclosure.

Also of importance is the pivoting of the fixture/troffer 200 about the pivot member 212 such that the fixture release mechanism 210 [see FIG. 1] is removably engaged with the install apparatus 400 such that the fixture/troffer 200 is held in place within the T-grid 10 on the surface 420.

Figure 3:
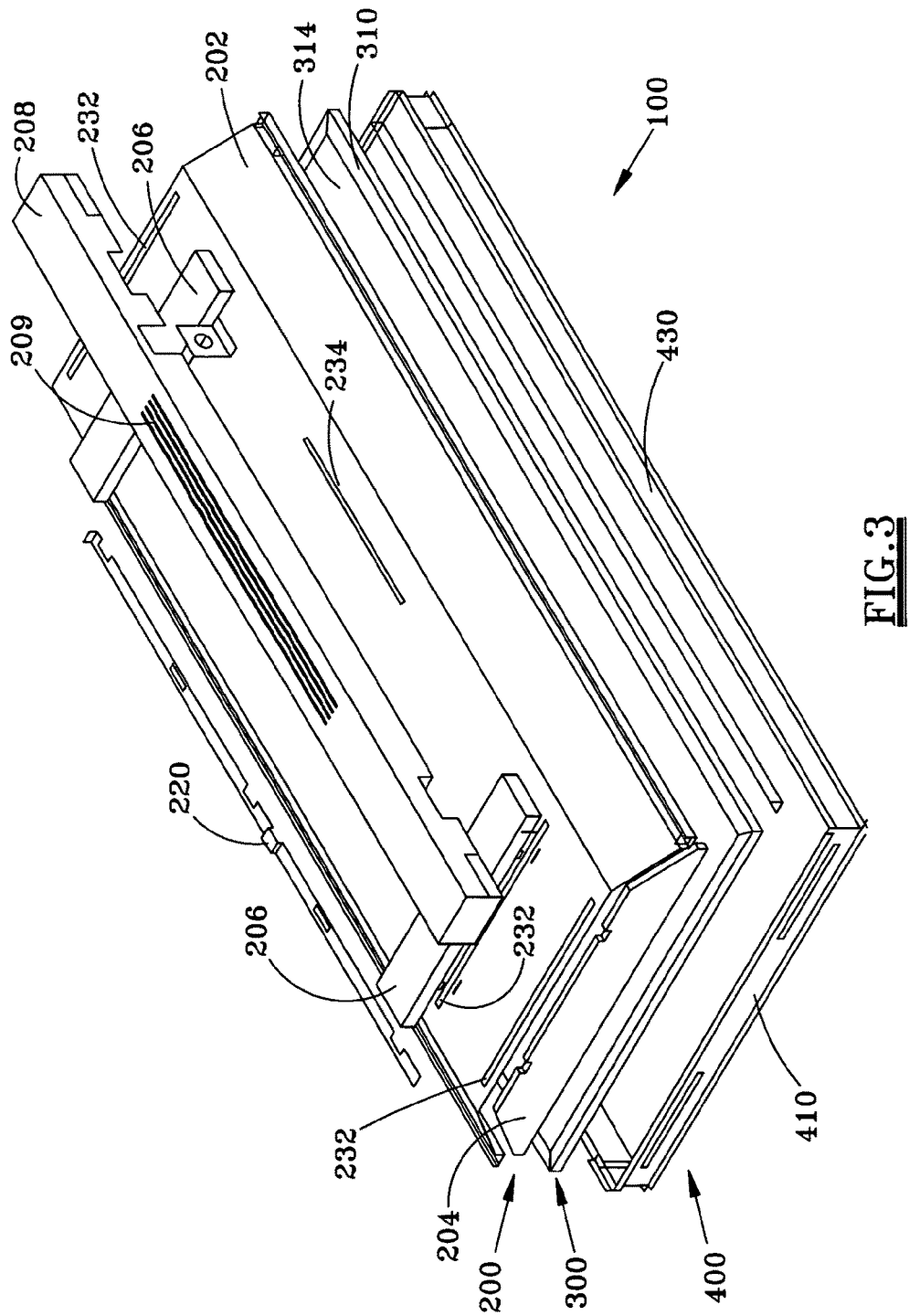
FIG. 3 is a perspective view of a preferred embodiment of the light fixture apparatus of the present disclosure showing the fixture/troffer, the Shadow Box™ trim and the install apparatus.

FIG. 3 is a perspective view of a preferred embodiment of the light fixture apparatus 100 of the present disclosure showing the fixture/troffer 200, the Shadow Box™ trim 300 and the install apparatus 400. The install apparatus 400 is illustrated with the lateral members 410 and the longitudinal members 430. The Shadow Box™ trim 300 is illustrated with the perimeter structure 310 and the display surface 314. The fixture/troffer 200 includes the base 202, the end plates 204, the lamp holder covers 206, the ballast cover 208 and the lock bar assembly 220. The base 202 has a plurality of tombstone adjustment slots 232 and one or more ballast slots 234. The tombstone adjustment slots 232 are provided in the form of knock-outs so that, depending on the length of the lamp to be used with the light fixture apparatus 100, the tombstone adjustment slots 232 corresponding to the lamp length used can be knocked out. Thus, it is appreciated by those skilled in the art that any lamp length or combination there of can be used with the light fixture apparatus 100 of the present disclosure. Similarly, the ballast adjustment slot 234 is provided for use with a ballast retainer [see FIG. 5] and ballast clip [not shown]. The ballast retainer provides that a conventional ballast having a projected portion can be slid under the ballast retainer for securing one end of the ballast. The ballast clip slideably engages the ballast adjustment slot 234 and the ballast for securing the ballast, regardless of size and shape, between the ballast retainer, the base 202 and the ballast clip. The ballast cover 208 has a ventilation grid 209.

Figure 4:
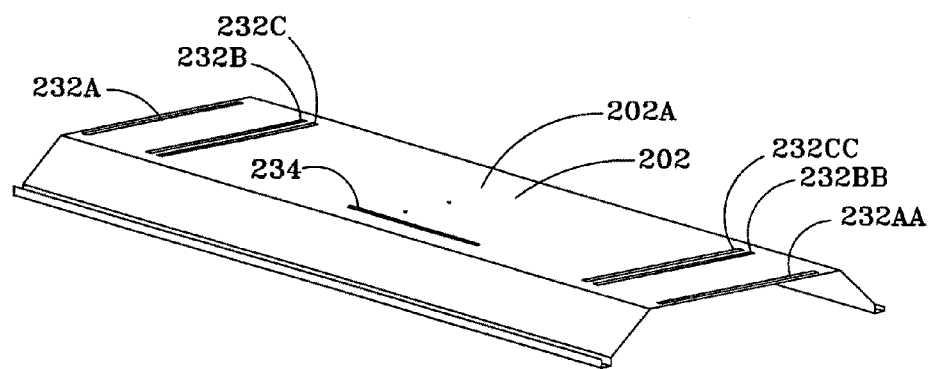
FIG. 4 is a perspective view of a preferred embodiment of the housing associated with the light fixture apparatus of the present disclosure.

FIG. 4 is a perspective view of a preferred embodiment of the housing or base 202 associated with the light fixture apparatus 100 of the present disclosure. FIG. 4 illustrates the ability of the light fixture apparatus 100 of the present disclosure to be adapted for use with any lamp and any ballast. The ability to adapt to any lamp is derived from the ability to locate the tombstones 205 [see FIG. 1] that hold the lamps at any location, and thus, for accepting a lamp of any dimension, regardless of length or radius. The tombstone adjustment slots 232A, 232AA are provided for holding tombstones at the greatest distance apart, and thus, for accepting a lamp of maximum length for the base 202 shown. The intermediate tombstone adjustment slots 232B, 232BB are provided for holding tombstones at an intermediate distance apart, and thus, for accepting a lamp of intermediate length for the base 202 shown. The tombstone adjustment slots 232C, 232CC are provided for holding tombstones at the shortest distance apart, and thus, for accepting a lamp of a minimum length for the base 202 shown. Since the tombstone adjustment slots 232 span the width of the base 202, tombstones 205 can be placed in any number across the base 202 with a lamp associated with each remote pair of tombstones 205. The limiting factor with respect to the number of lamps that can be adapted for use in the light fixture apparatus 100 of the present disclosure is that the sum of the diameters of all the lamps is less that the length of the respective tombstone adjustment slots 232. A ballast adjustment slot 234 is illustrated in the convexed surface 202A to operate in a similar manner as do the tombstone adjustment slots 232.

Figure 5:
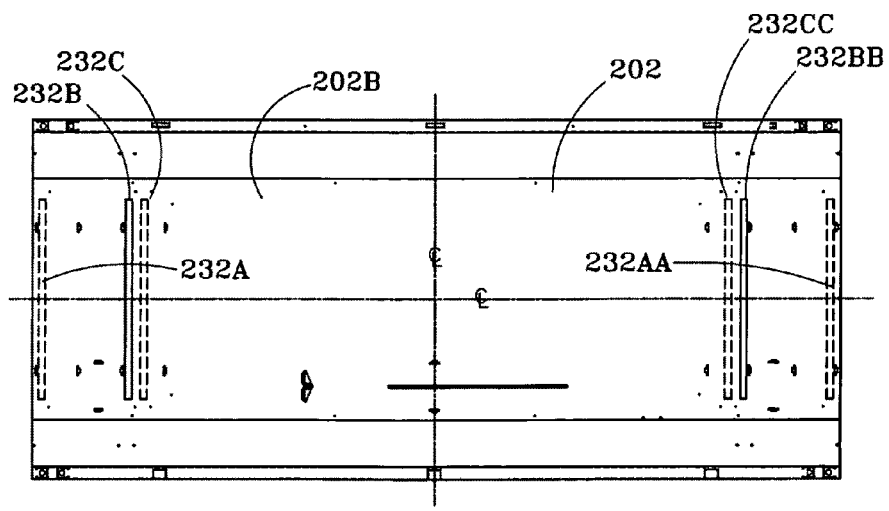
FIG. 5 is a plan view of the back side a preferred embodiment of the housing associated with the light fixture apparatus of the present disclosure.

FIG. 5 is a plan view of the preferred embodiment of the concaved surface 202B of the housing 202 associated with the light fixture apparatus 100 of the present disclosure as illustrated in FIG. 4. The tombstone adjustment slots 232A, 232AA, 232C, 232CC for the maximum length lamp and the minimum length lamps are illustrated as knock-outs. The tombstone adjustment slots 232B, 232BB for the intermediate length lamps are illustrated as slots ready to accept the tombstones 205 which are secured by the tombstone holders 207 as illustrated in FIG. 2. The ballast adjustment slot 234 is provided for use with a ballast retainer [in line with the ballast adjustment slot 234] and the ballast clip [not shown]. The ballast retainer provides that a conventional ballast having a projected portion can be slid under the ballast retainer for securing one end of the ballast. The ballast clip slideably engages the ballast adjustment slot 234 and the ballast for securing the ballast, regardless of size and shape, between the ballast retainer, the base 202 and the ballast clip. As is appreciated by those skilled in the art, the ballast clip can be any configuration which effects the removable engagement of the ballast with the ballast retainer, the base 202 and the ballast clip.

Figure 6A:
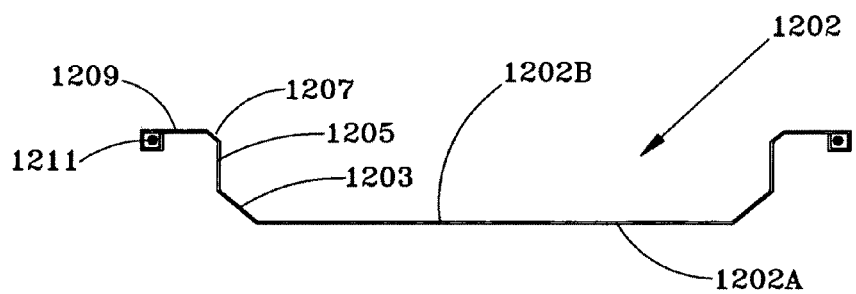
FIG. 6A is an end view of another preferred embodiment of the housing associated with the light fixture apparatus of the present disclosure.
Figure 6:
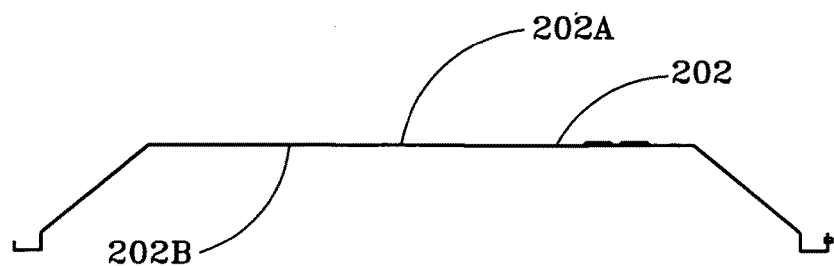
FIG. 6 is an end view of a preferred embodiment of the housing associated with the light fixture apparatus of the present disclosure.
Figure 8:
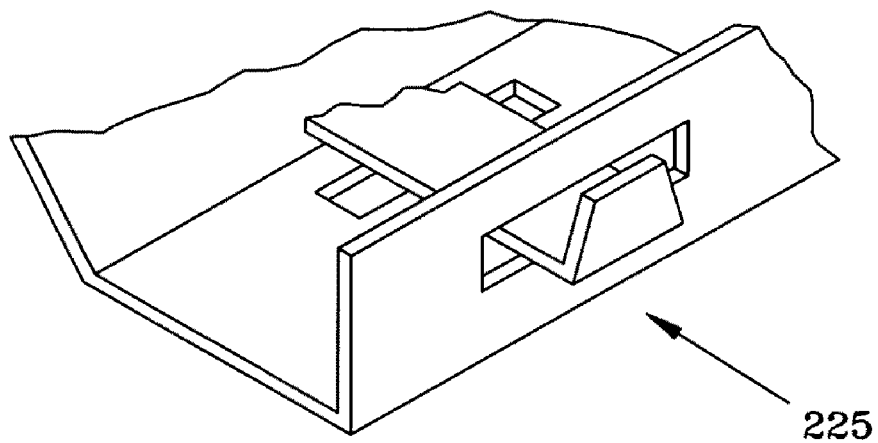
FIG. 8 is a perspective view of a preferred embodiment of latch mechanism associated with the light fixture apparatus of the present disclosure.
Figure 9:
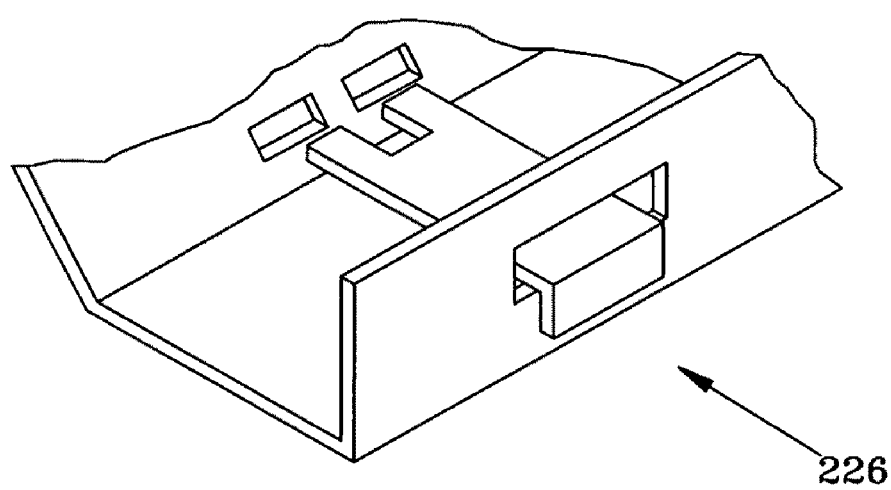
FIG. 9 is a perspective view of another preferred embodiment of latch mechanism associated with the light fixture apparatus of the present disclosure.

FIG. 6 is an end view of a preferred embodiment of the housing 202 associated with the light fixture apparatus 100 of the present disclosure. The housing 202 is illustrated to view the convexed portion 202A of the housing 202 with the concaved portion 202B of the housing 202. The extremities illustrated in FIG. 6 are illustrated in FIGS. 8 and 9 to better illustrate possible release mechanisms.

Figure 5A:
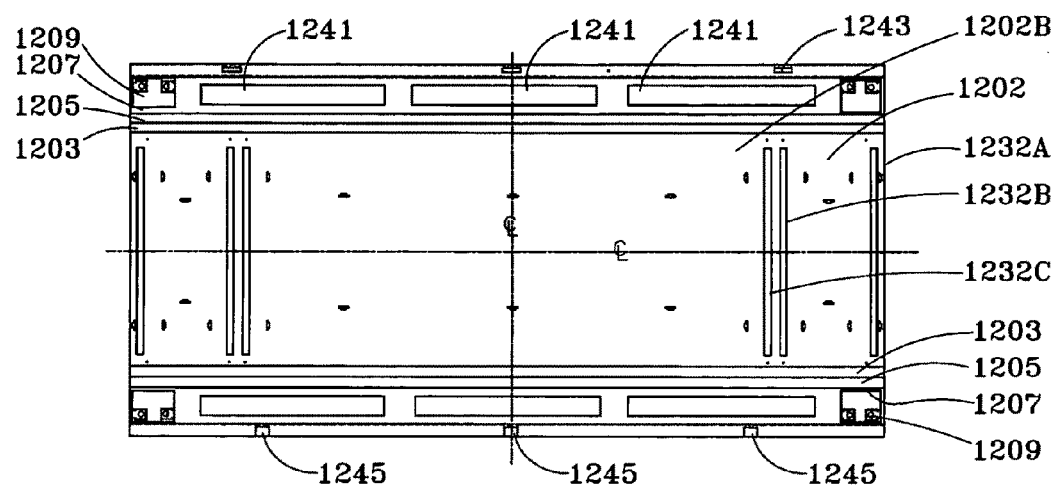
FIG. 5A is a plan view of the back side another preferred embodiment of the housing associated with the light fixture apparatus of the present disclosure.

FIG. 5A is a plan view of the back side another preferred embodiment of the housing 1202 associated with the light fixture apparatus of the present disclosure. The housing 1202 comprises a concaved portion 1202B, a first angled portion 1203, a second angled portion 1205, a third angled portion 1207, a planer portion 1209 and a flat portion 1211. The concaved portion 1202B has therein a plurality of tombstone adjustment slots 1232A, 1232AA, 1232B, 1232BB, 1232C, 1232CC. The planer portion 1209 comprises one or more knock-outs 1241. Also, the planer portion 1209 comprises one or more T-shaped apertures 1243 that are engaging and/or pivoting points for engaging elements. Further, the planer portion 1209 comprises one or more apertures 1245.

FIG. 6A is an end view of another preferred embodiment of the housing 1202 associated with the light fixture apparatus of the present disclosure. The housing 1202 comprises a concaved portion 1202B, a convexed portion 1202A, a first angled portion 1203, a second angled portion 1205, a third angled portion 1207, a planer portion 1209 and a flat portion 1211.

Figure 7:
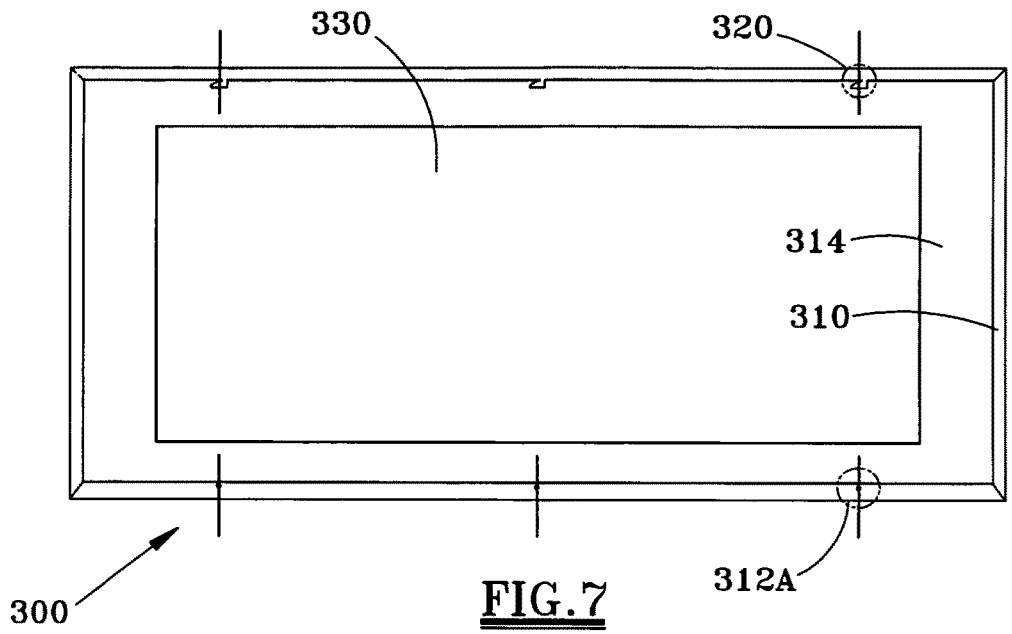
FIG. 7 is a plan view of a preferred embodiment of the Shadow Box™ trim associated with the light fixture apparatus of the present disclosure.

FIG. 7 is a plan view of a preferred embodiment of the Shadow Box™ trim 300 associated with the light fixture apparatus 100 of the present disclosure. The Shadow Box™ trim 300 comprises a perimeter structure 310, a display surface 314, a light opening 330A, a pivot member 312A and an engaging mechanism 320.

The Shadow Box™ trim 300 can be removed and attached to the light fixture 100 without tools or attachment mechanisms. Any Shadow Box™ trim 300 is easily interchanged with another Shadow Box™ trim 300. The Shadow Box™ trim 300 provides decorative trim which can be made of various materials, colors, textures and designs to depict corporate logos or other branding or advertising designs. The Shadow Box™ trim 300 may be, but not required to be, rotated and laid into place so as to be removed and replaced without being lifted above the T-grid. The Shadow Box™ trim 300 can also provide a means for an indirect lighting apparatus. Further, the Shadow Box™ trim 300 can be adapted for use with any fixture.

More particularly, but without limitation, the Shadow Box™ trim 300 can be plain, bear a design, bear a picture, bear a logo, bear a particular branding, or convey advertising, all referred to simply as the design. The Shadow Box™ trim 300 provides that the design therein can be illuminated. The illumination of the design in the Shadow Box™ trim 300 can be provided by the lamps associated with the light fixture. Also, the design in the Shadow Box™ trim 300 can be illuminated by an alternate light source. Examples of such alternate light sources are, without limitation, LEDs, lasers, cold cathode devices, CFLs and the like. The design in the Shadow Box™ trim 300 can be displayed in different colors. The coloring of the design can be achieved by using colored mylar film, colored LEDs, prisms, or the like. The Shadow Box™ trim 300 has quick release-engaging mechanism 320 to easily pivot, remove and replace the Shadow Box™ trim 300.

FIG. 8 is a perspective view of a preferred embodiment of latch mechanism 225 associated with the light fixture apparatus 100 of the present disclosure.

FIG. 9 is a perspective view of another preferred embodiment of latch mechanism 226 associated with the light fixture apparatus 100 of the present disclosure.

FIG. 10 is a perspective view of a preferred embodiment of the ballast cover 208 associated with the light fixture apparatus 100 of the present disclosure. The ballast cover 208 is an elongate member such that any size ballast can be covered. The ballast cover 208 has open knock-outs 208A for accepting the tombstone holder cover for the lamp holders 206. Further, the ballast cover 208 has closed knock-outs 208B which are available for knocking out and thereafter for accepting the tombstone holder cover for the lamp holders 206. Typically, the ends of the ballast cover 208 are closed. Also, the ballast cover 208 has an opening between the open knock-outs 208A for accepting power from a remote power source.

FIG. 11 is a perspective view of a preferred embodiment of ballast cover 208 associated with the light fixture apparatus 100 of the present disclosure that provides for the venting of heat from the ballast cover 208 by a ventilation grid 209. The ballast cover 208 has open knock-outs 208A for accepting the tombstone holder cover for the lamp holders 206. Further, the ballast cover 208 has closed knock-outs 208B which are available for knocking out and thereafter for accepting the tombstone holder cover for the lamp holders 206.

Figure 12:
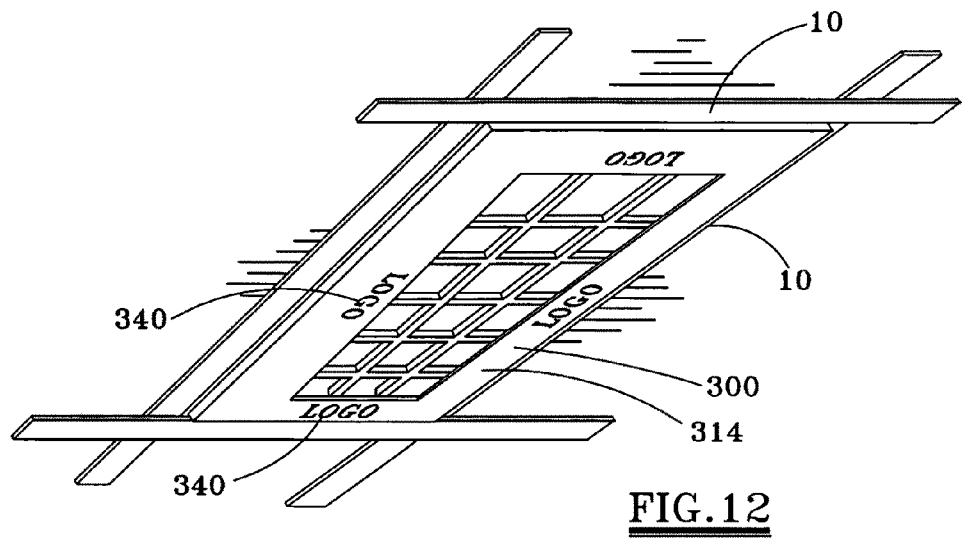
FIG. 12 is a perspective view of a preferred embodiment of the light fixture apparatus of the present disclosure engaged with a T-grid as seen from below illustrating the promotional use of a logo with the Shadow Box™ trim.

FIG. 12 is a perspective view of a preferred embodiment of the light fixture apparatus 100 of the present disclosure engaged with a T-grid 10 as seen from below illustrating the promotional use of a logo 340 with the Shadow Box™ trim 300. The logo 340 is in the display surface 314 of the Shadow Box™ trim 300. The logo 340 can be lighted by the lamps in the fixture/troffer 200, or alternately, can be lighted by auxiliary means so the logo 340 remains illuminated when the lamps in the light fixture apparatus 100 are off.

Figure 13:
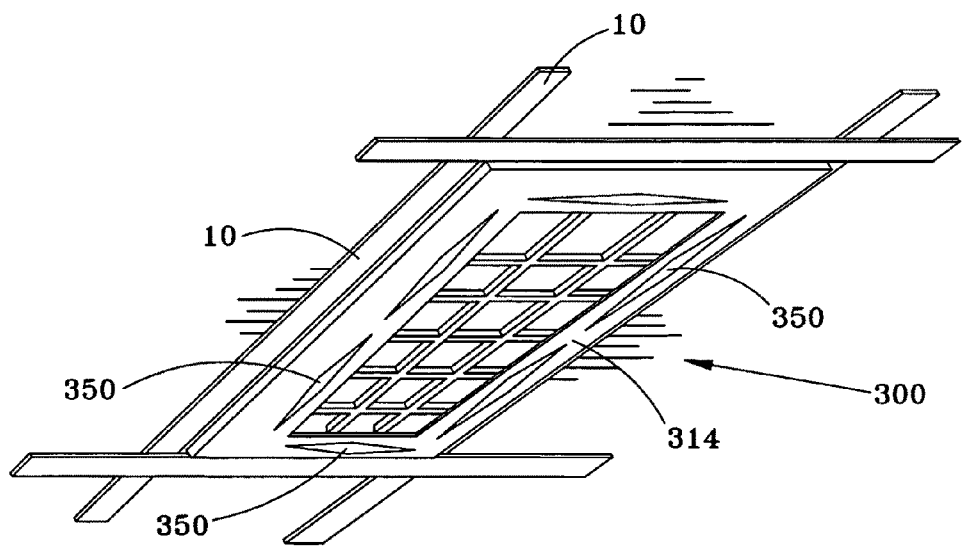
FIG. 13 is a perspective view of a preferred embodiment of the light fixture apparatus of the present disclosure engaged with a T-grid as seen from below illustrating the promotional use of a design with the Shadow Box™ trim.

FIG. 13 is a perspective view of a preferred embodiment of the light fixture apparatus 100 of the present disclosure engaged with a T-grid 10 as seen from below illustrating the promotional use of a design 350 with the Shadow Box™ trim 300. The design 350 is in the display surface 314 of the Shadow Box™ trim 300. The design 350 can be lighted by the lamps in the fixture/troffer 200, or alternately, can be lighted by auxiliary means so the design 350 remains illuminated when the lamps in the light fixture apparatus 100 are off.

Figure 14:
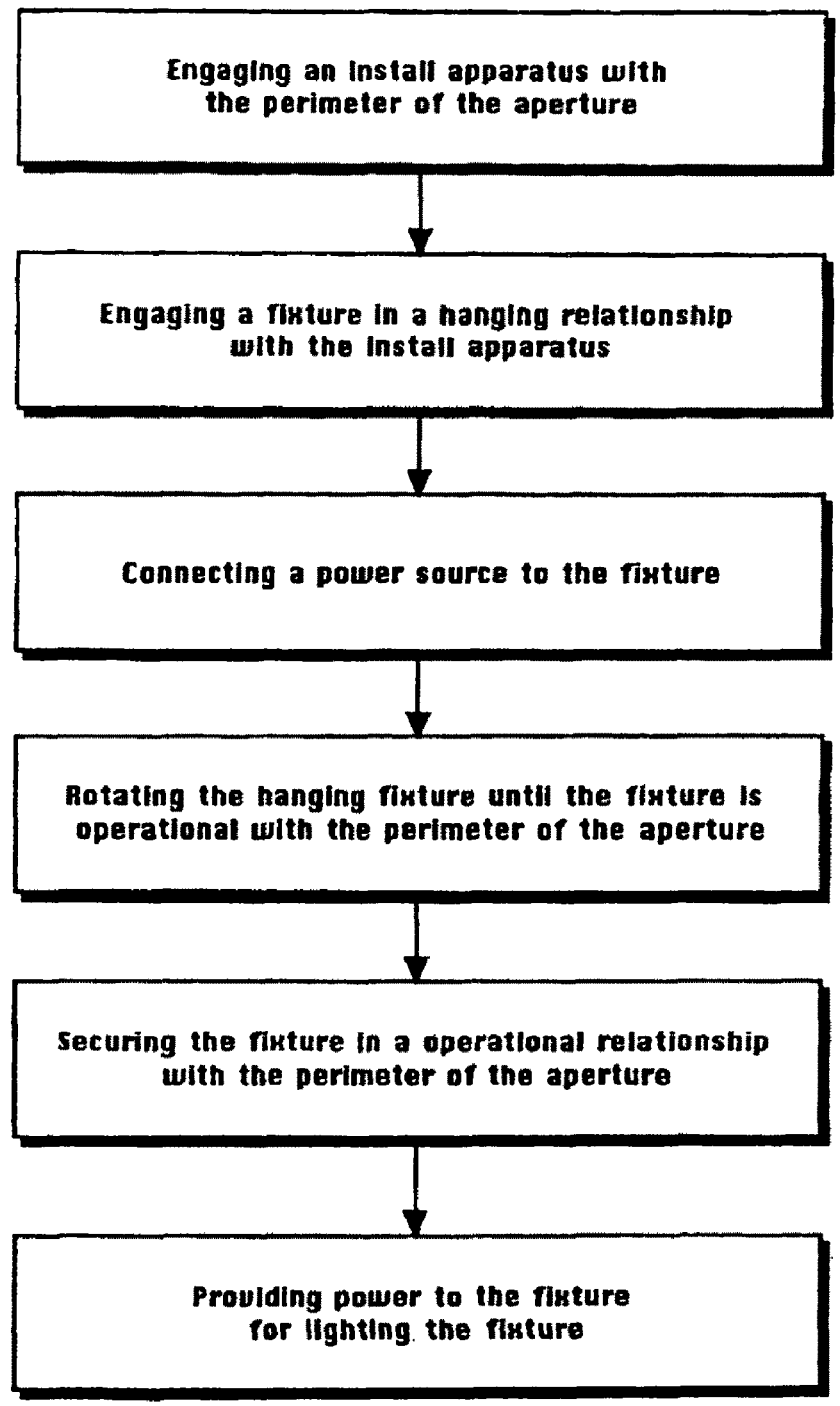
FIG. 14 is a flow chart illustrating a preferred embodiment of the method of installing a light fixture as practiced by the present disclosure.

FIG. 14 is a flow chart illustrating a preferred embodiment of the method of installing a light fixture as practiced by the present disclosure. The method of installing a light fixture as practiced by the present disclosure into an aperture in a ceiling, wall or box where the aperture is defined by a perimeter comprises the steps of engaging an install apparatus with the perimeter of the aperture, engaging a fixture in a hanging relationship with the install apparatus, connecting a power source to the fixture, rotating the hanging fixture until the fixture is operational with the perimeter of the aperture, securing the fixture in a operational relationship with the perimeter of the aperture, and providing power to the fixture for lighting the fixture.

Figure 15:
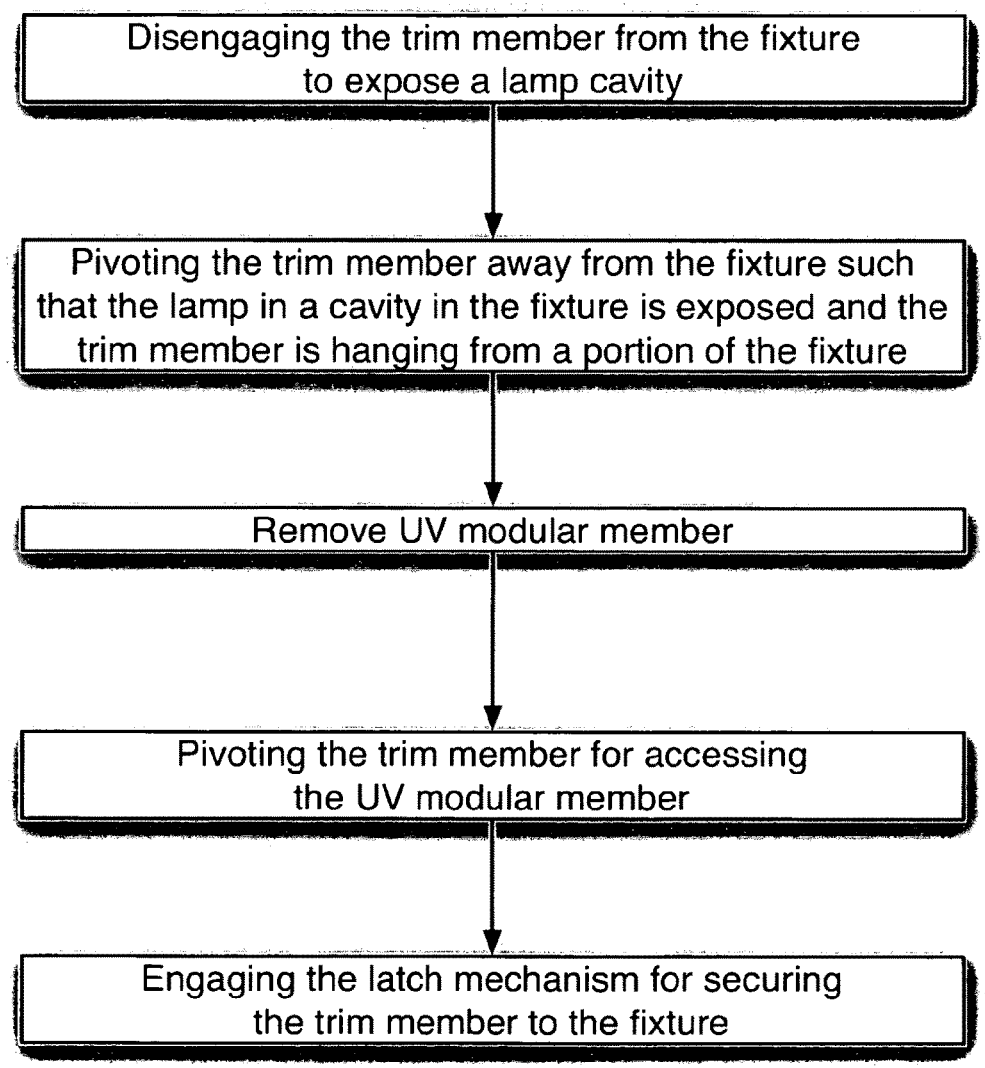
FIG. 15 is a flow chart illustrating a preferred embodiment of the method of changing a lamp as practiced by the present disclosure.

FIG. 15 is a flow chart illustrating a preferred embodiment of the method of changing a lamp in a light fixture as practiced by the present disclosure. The method of changing a lamp in a light fixture as practiced by the present disclosure wherein the light fixture is engaged in a pivotal relationship by a trim member comprising the steps of disengaging the trim member from the fixture to expose a lamp cavity, pivoting the trim member away from the fixture such that the lamp in a cavity in the fixture is exposed and the trim member is hanging from a portion of the fixture, removing the old lamp from the cavity, and engaging a new lamp in the cavity without displacing any other lamp or component, pivoting the trim member for securing the lamp in the cavity, and engaging the latch mechanism for securing the trim member to the fixture.

Figure 16:
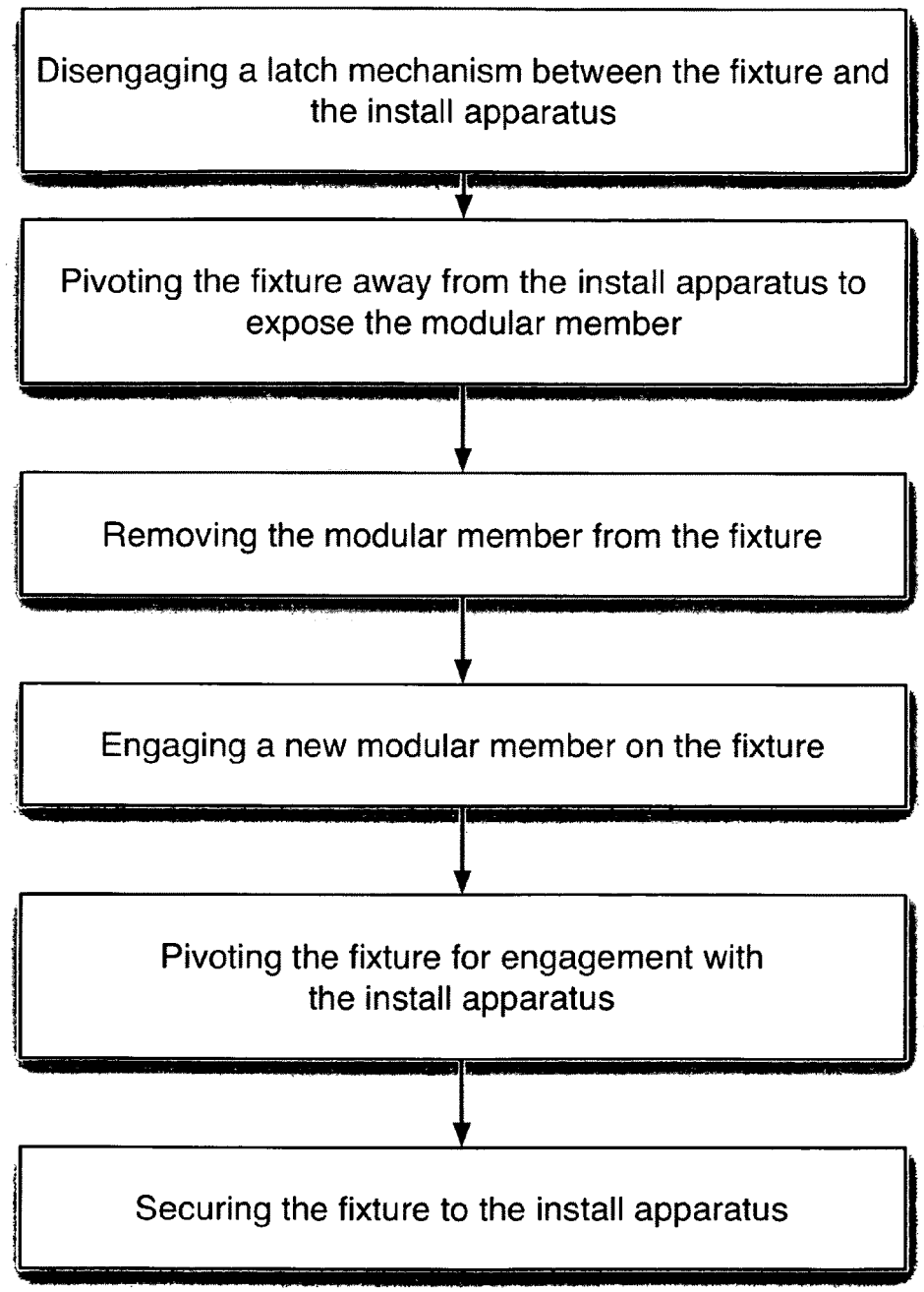
FIG. 16 is a flow chart illustrating a preferred embodiment of the method of changing a ballast as practiced by the present disclosure.

FIG. 16 is a flow chart illustrating a preferred embodiment of the method of changing a ballast as practiced by the present disclosure. The method of changing a ballast in a light fixture as practiced by the present disclosure wherein the light fixture is engaged in a pivotal relationship with an install apparatus comprising the steps of disengaging a latch mechanism between the fixture and the install apparatus, pivoting the fixture away from the install apparatus to expose the ballast area, removing the old ballast from the fixture, engaging a new ballast on the fixture, pivoting the fixture for engagement with the install apparatus, and securing the fixture to the install apparatus.

Figure 17:
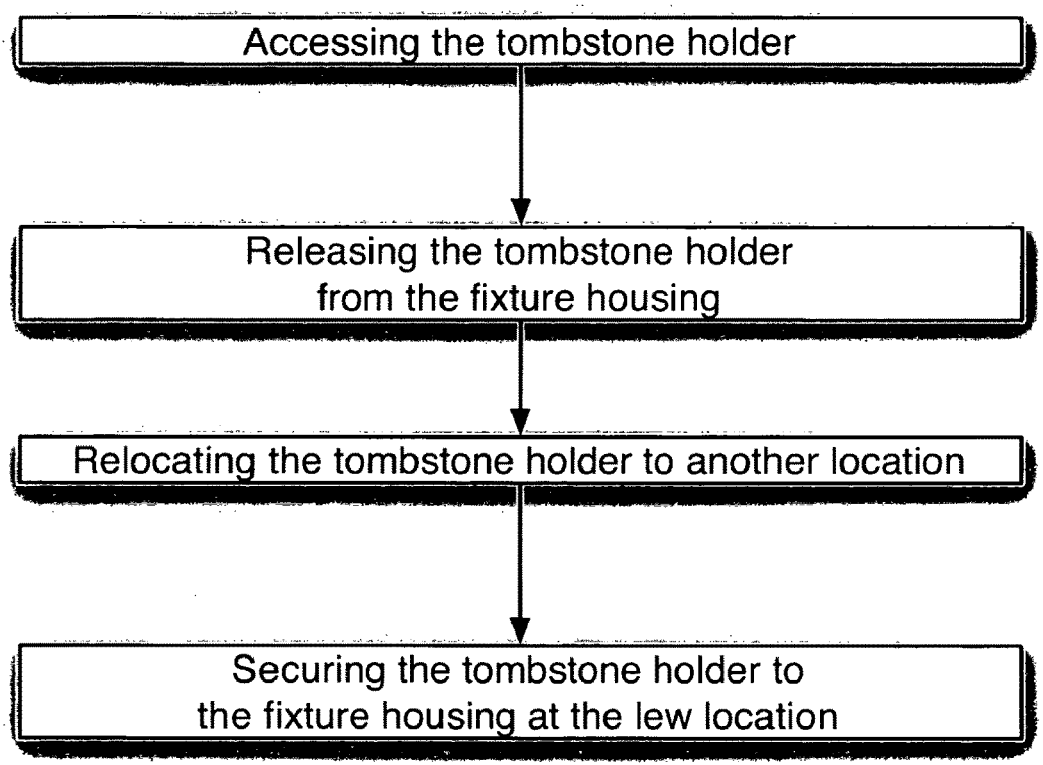
FIG. 17 is a flow chart illustrating a preferred embodiment of the method of changing the location of a tombstone holder with respect to a fixture as practiced by the present disclosure.

FIG. 17 is a flow chart illustrating a preferred embodiment of the method of changing the location of a tombstone holder with respect to a fixture for changing lamps having different lengths as practiced by the present disclosure. The method of changing the location of a tombstone holder with respect to a fixture for changing lamps having different lengths comprising the steps of accessing the tombstone holder, releasing the tombstone holder from the fixture housing, relocating the tombstone holder to another location, and securing the tombstone holder to the fixture housing at the new location.

Figure 18:
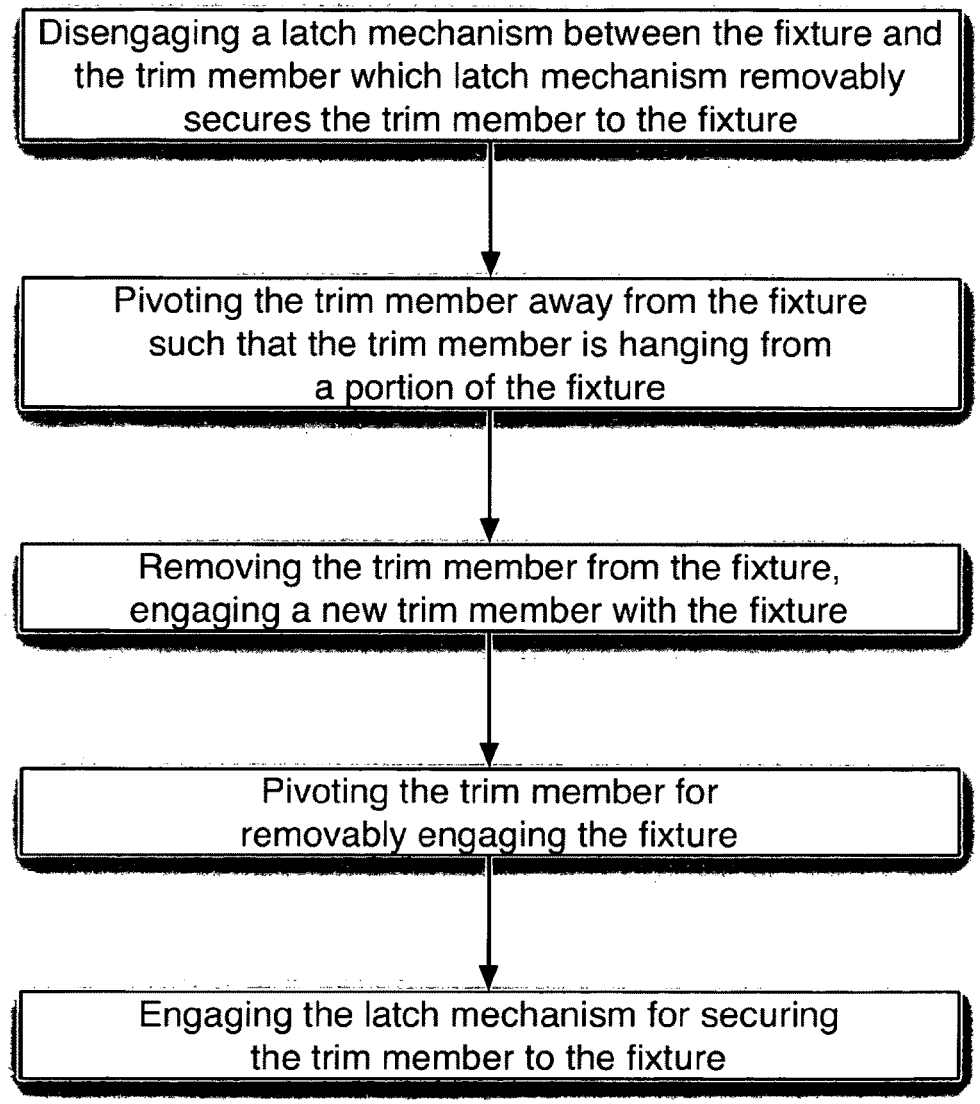
FIG. 18 is a flow chart illustrating a preferred embodiment of the method of using a shadow box with a light fixture as practiced by the present disclosure.

FIG. 18 is a flow chart illustrating a preferred embodiment of the method of using a Shadow Box™ trim or trim member with a light fixture as practiced by the present disclosure. The method of using a Shadow Box™ trim or trim member with a light fixture as practiced by the present disclosure wherein the light fixture is engaged in a pivotal relationship by a trim member comprising the steps of disengaging a latch mechanism between the fixture and the trim member which latch mechanism removably secures the trim member to the fixture, pivoting the trim member away from the fixture such that the trim member is hanging from a portion of the fixture, removing the trim member from the fixture, engaging a new trim member with the fixture, pivoting the trim member for removably engaging the fixture, and engaging the latch mechanism for securing the trim member to the fixture.

Figure 19:
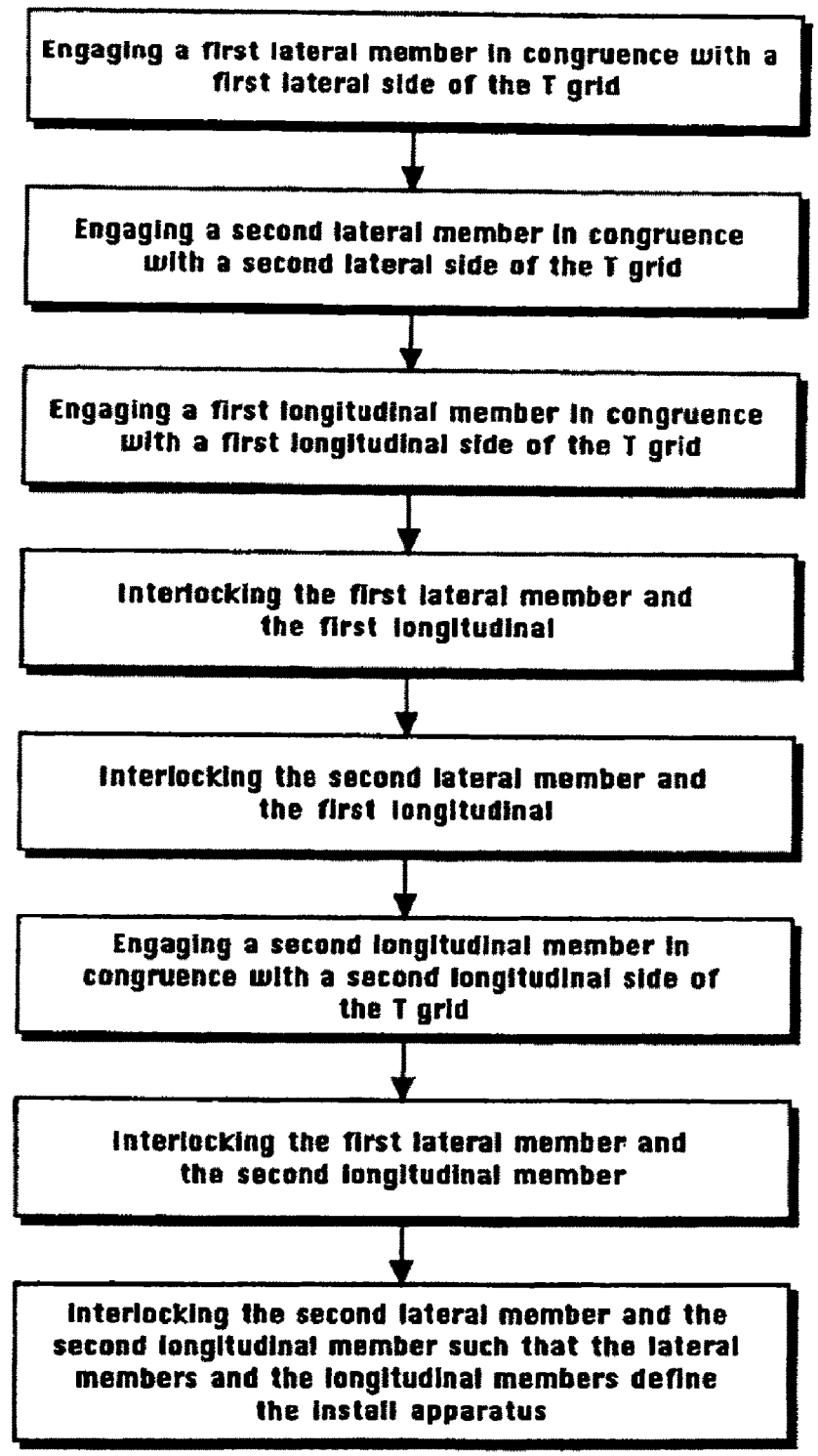
FIG. 19 is a flow chart illustrating a preferred embodiment of the method of installing an install apparatus as practiced by the present disclosure.

FIG. 19 is a flow chart illustrating a preferred embodiment of the method of installing an install apparatus in a T-grid as practiced by the present disclosure. The method of installing an install apparatus in a T-grid as practiced by the present disclosure comprising the steps of engaging a first lateral member in congruence with a first lateral side of the T-grid, engaging a second lateral member in congruence with a second lateral side of the T-grid, engaging a first longitudinal member in congruence with a first longitudinal side of the T-grid, interlocking the first lateral member and the first longitudinal, interlocking the second lateral member and the first longitudinal, engaging a second longitudinal member in congruence with a second longitudinal side of the T-grid, interlocking the first lateral member and the second longitudinal member, interlocking the second lateral member and the second longitudinal member such that the lateral members and the longitudinal members define the install apparatus.

Figure 20:
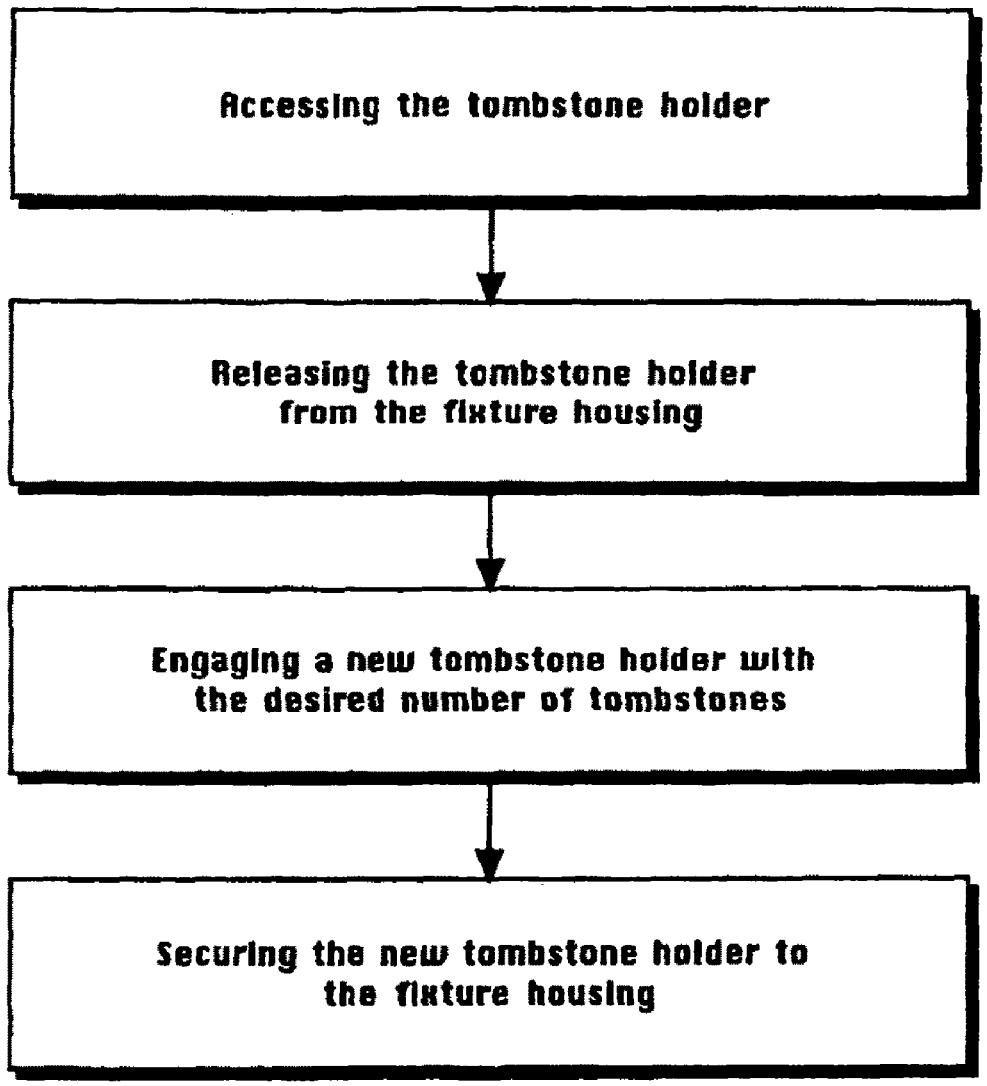
FIG. 20 is a flow chart illustrating a preferred embodiment of the method of changing the lamp configurations or the lamp quantities as practiced by the present disclosure.

FIG. 20 is a flow chart illustrating a preferred embodiment of the method of changing the lamp configurations or the lamp quantities as practiced by the present disclosure. The method of changing the lamp configurations or the lamp quantities comprises the steps of accessing the tombstone holder, releasing the tombstone holder from the fixture housing, engaging a new tombstone holder with the desired number of tombstones and securing the new tombstone holder to the fixture housing.

Figure 21:
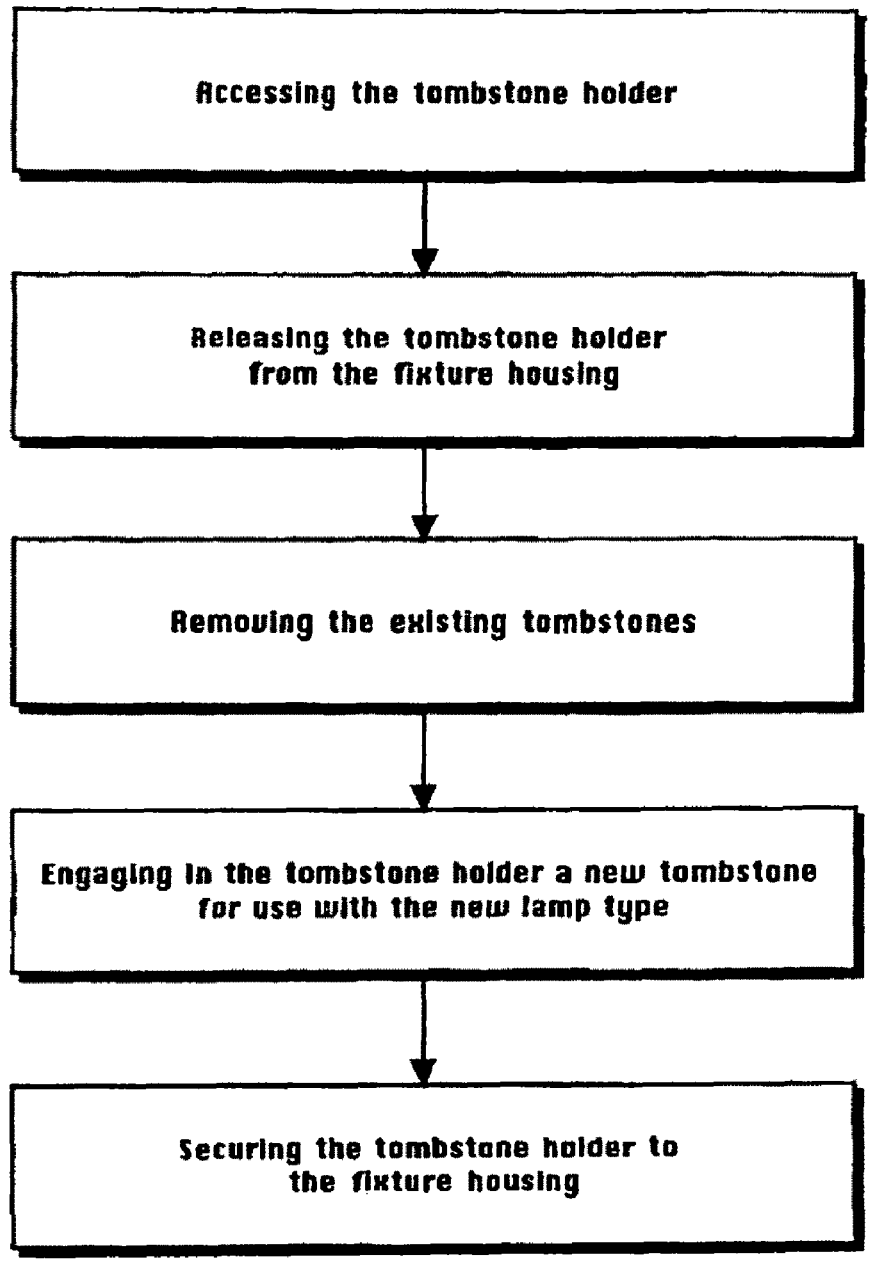
FIG. 21 is a flow chart illustrating a preferred embodiment of the method of changing the lamp types as practiced by the present disclosure.

FIG. 21 is a flow chart illustrating a preferred embodiment of the method of changing the lamp types as practiced by the present disclosure. The method of changing the lamp types comprises the steps of accessing the tombstone holder, releasing the tombstone holder from the fixture housing, removing the existing tombstone, engaging in the tombstone holder a new tombstone for use with the new lamp type and securing the tombstone holder to the fixture housing.

Figure 22:
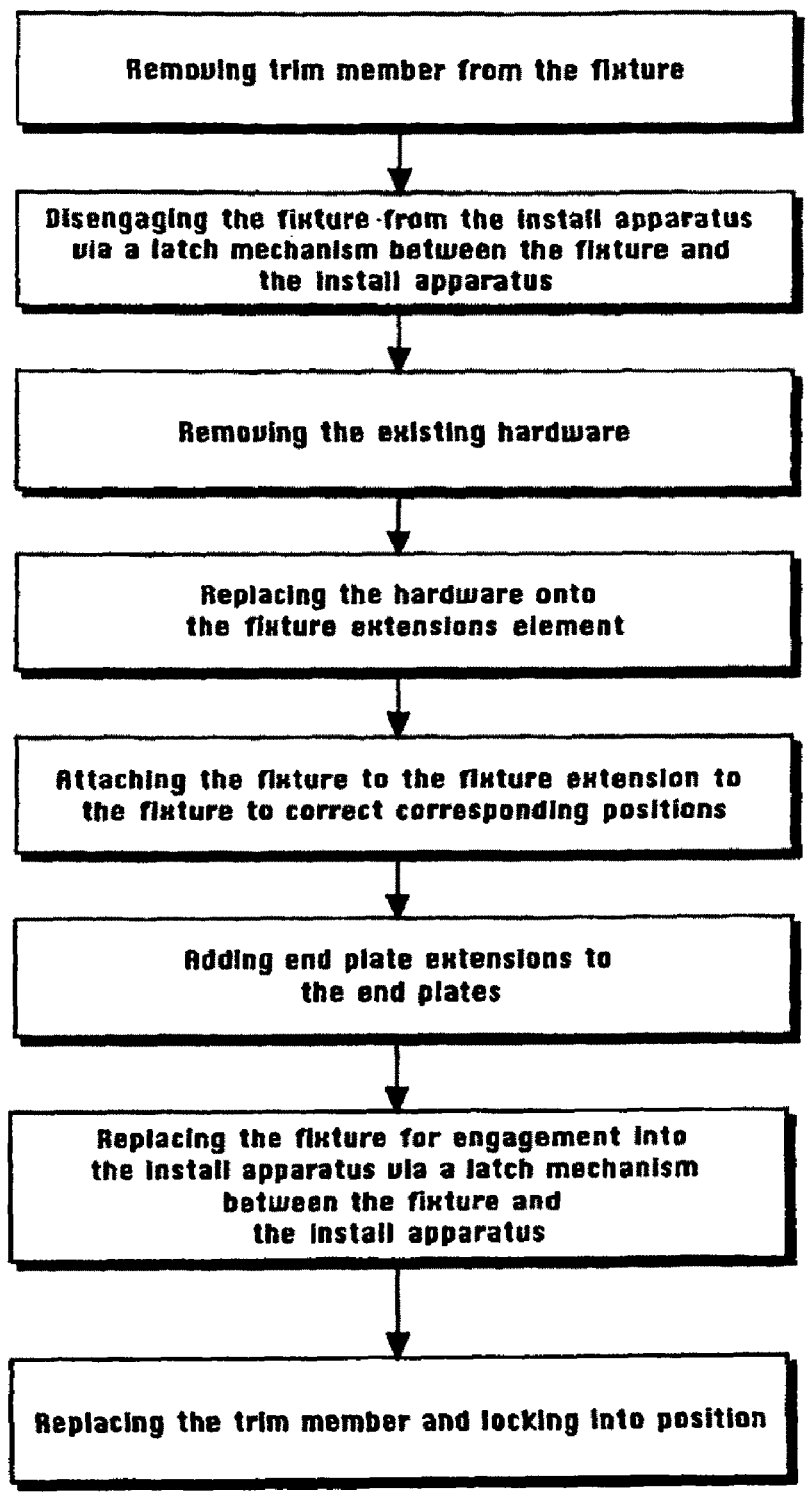
FIG. 22 is a flow chart illustrating a preferred embodiment of the method of using a light fixture extension as practiced by the present disclosure.

FIG. 22 is a flow chart illustrating a preferred embodiment of the method of using a light fixture extension as practiced by the present disclosure. The method of using a light fixture extension as practiced by the present disclosure for placement into an aperture in a ceiling, wall or box where the aperture is defined by a perimeter comprising the steps of removing a trim member from the fixture, disengaging the fixture from the install apparatus via a latch mechanism between the fixture and the install apparatus, removing the existing hardware, replacing the hardware onto the fixture extensions, attaching the fixture to the fixture extensions to the correct corresponding positions, adding an end plate extension to the end plates, replacing the fixture for engagement into the install apparatus via a latch mechanism between the fixture and the install apparatus, and replacing the trim member and locking into position.

Figure 23:
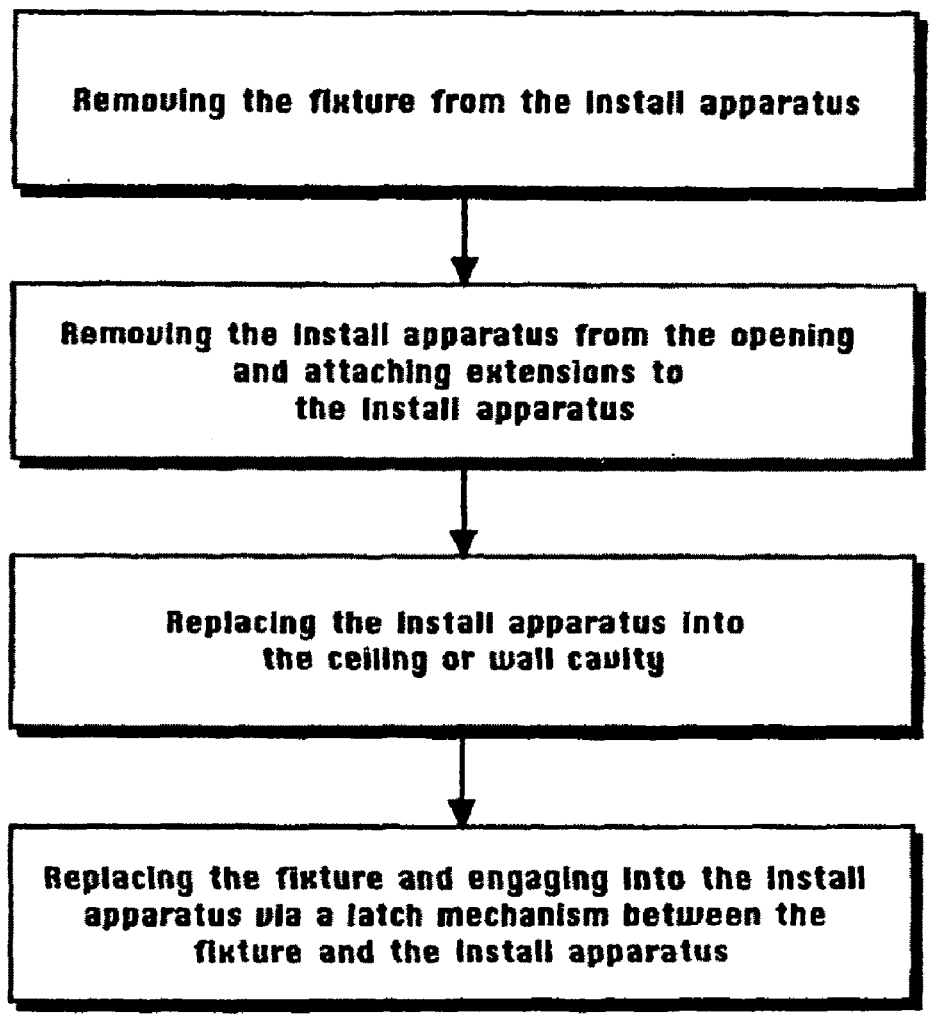
FIG. 23 is a flow chart illustrating a preferred embodiment of the method of using an install apparatus extension as practiced by the present disclosure.

FIG. 23 is a flow chart illustrating a preferred embodiment of the method of using an install apparatus extension as practiced by the present disclosure. The method of using an install apparatus extension as practiced by the present disclosure for placement into an aperture in a ceiling, wall or box where the aperture is defined by a perimeter comprises the steps of removing the fixture from the install apparatus, removing the install apparatus from the opening and attaching extensions to the install apparatus, replacing the install apparatus into the ceiling or wall cavity, and replacing the fixture and engaging into the install apparatus via a latch mechanism between the fixture and the install apparatus.

Figure 24:
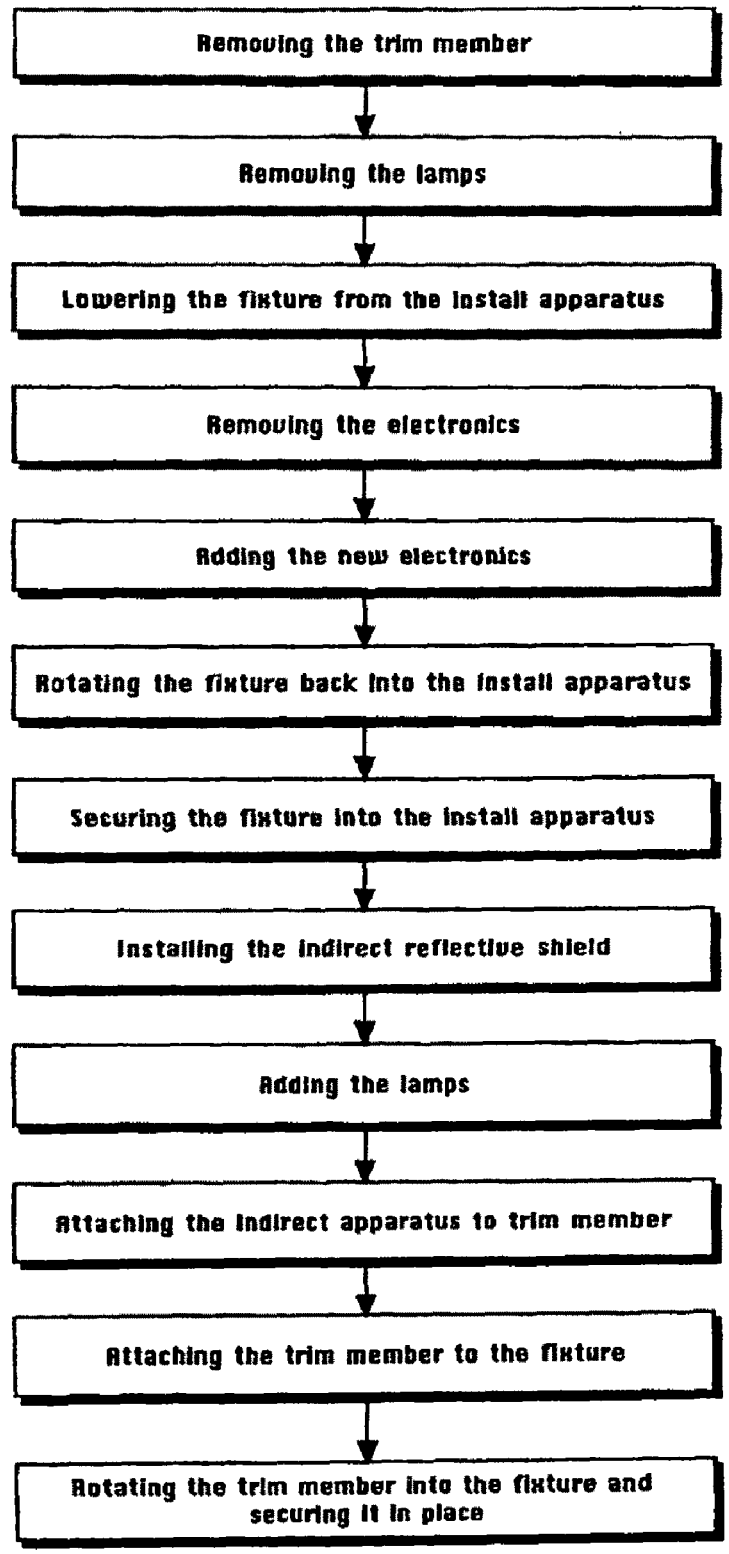
FIG. 24 is a flow chart illustrating a preferred embodiment of the method of adapting a light fixture as practiced by the present disclosure for casting indirect light.
Figure 25:
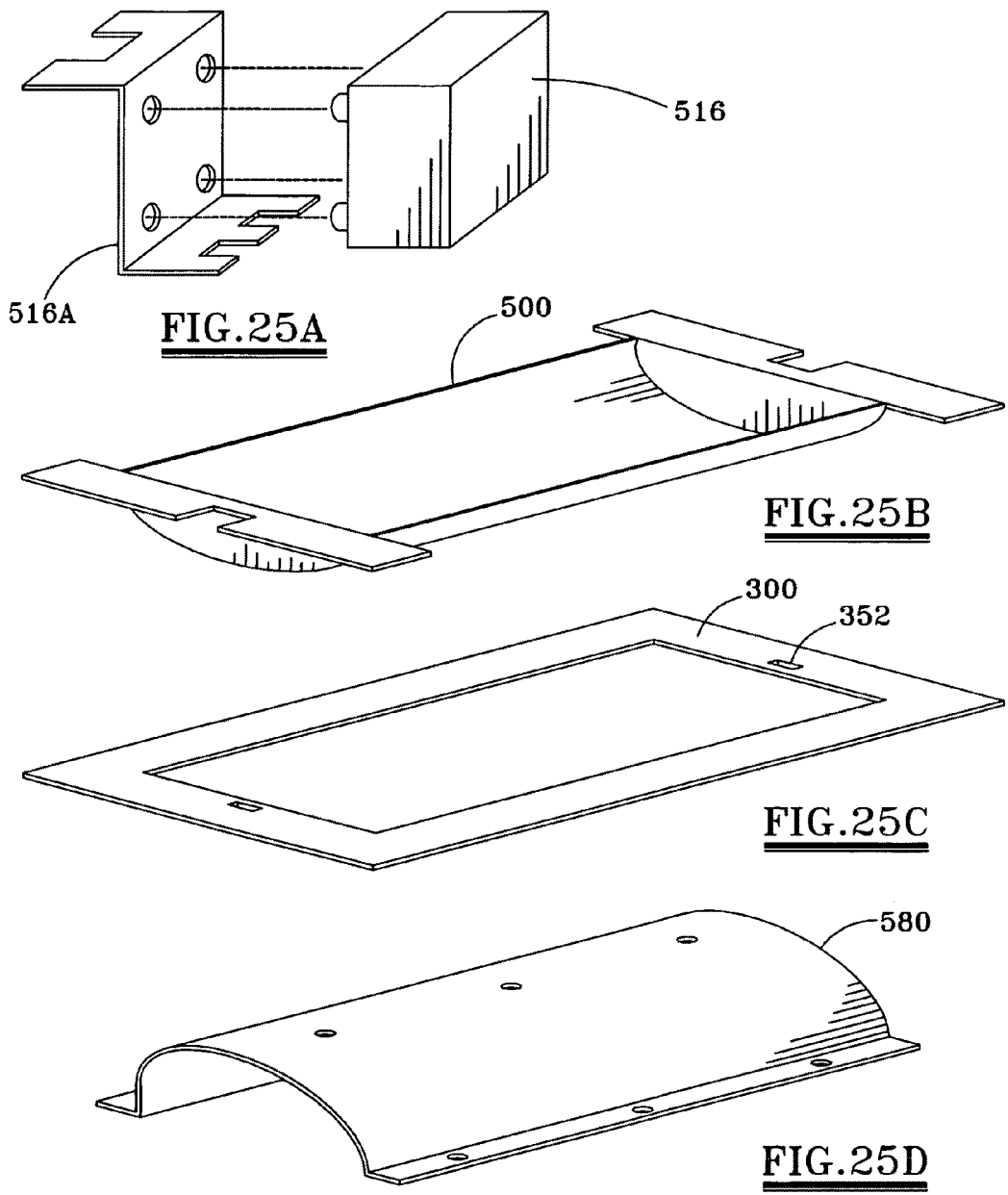
FIGS. 25A, 25B, 25C, 25D are perspective views of a preferred embodiment of an indirect lighting trim for use with the light fixture apparatus of the present disclosure.

FIG. 24 is a flow chart illustrating a preferred embodiment of the method of adapting a light fixture as practiced by the present disclosure for casting indirect light. The method of adapting a light fixture as practiced by the present disclosure for casting indirect light comprising the steps of, removing the trim member, removing the lamps, lowering the fixture from the install apparatus, removing the electronics, adding the new electronics, rotating the fixture back into the install apparatus, securing the fixture into the install apparatus, installing the indirect reflective shield, adding the lamps, attaching the indirect apparatus to trim member, attaching the trim member to the fixture, and rotating the trim member into the fixture and securing it in place.

FIGS. 25A, 25B, 25C, 25D are perspective views of a preferred embodiment of an indirect lighting trim 500 for use with the light fixture apparatus 100 of the present disclosure. FIGS. 25A, 25B, 25C, 25D illustrate the indirect lighting trim 500 for converting the light fixture apparatus 100 of the present disclosure into an indirect lighting fixture. The tombstone holder extension 516A is inserted into the desired lamp length slot 232B, 232BB [see FIG. 4] allowing the lamps 12 to be positioned to the desired heights within the fixture/troffer 200 [see FIG. 1]. The lamp holders 205 are inserted into the tombstone holder extension 516A before the tombstone holder extension cover 516 is attached. The indirect lighting trim 500 is placed onto the Shadow Box™ trim 300 and secured into place with a clip device 352. The indirect reflective shield 580 is inserted into the fixture/troffer 200 and secured into place before closing the Shadow Box™ trim 300 with the indirect lighting trim 500 attached.

Figure 26:
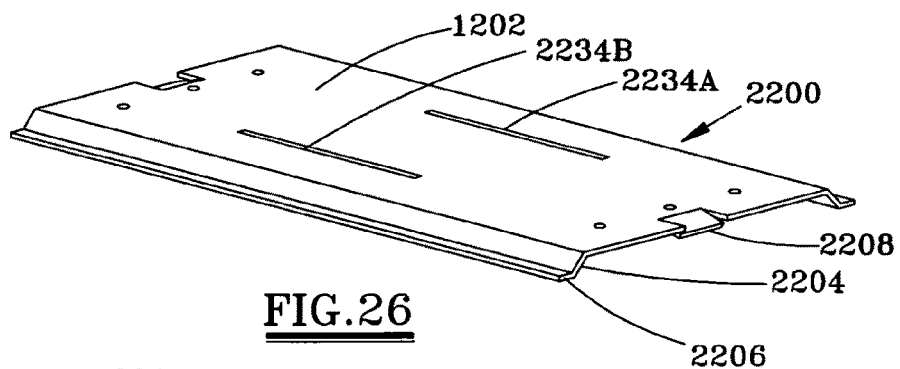
FIG. 26 is a perspective view of a preferred embodiment of a ballast rail of the present disclosure.

FIG. 26 is a perspective view of a preferred embodiment of a ballast rail 2200 of the present disclosure. The ballast rail 2200 comprises a planar portion 2202, an offset portion 2204, a lip portion 2206 and a beveled portion 2208. The planar portion 2202 has one or more ballast adjustment slots 2234A, 2234B for removeably securing a ballast to the ballast rail 2200.

Figure 27:
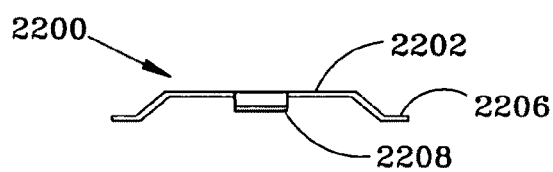
FIG. 27 is an end view of the preferred embodiment of a ballast rail of the present disclosure as illustrated in FIG. 26.

FIG. 27 is an end view of the preferred embodiment of the ballast rail 2200 of the present disclosure as illustrated in FIG. 26. The ballast rail 2200 has a planar portion 2202, an offset portion 2204 and a lip portion 2206 and a beveled portion 2208.

Figure 28:
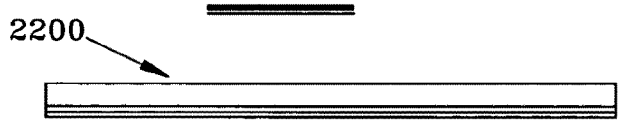
FIG. 28 is a longitudinal view of the preferred embodiment of a ballast rail of the present disclosure as illustrated in FIG. 26.

FIG. 28 is a longitudinal view of the preferred embodiment of the ballast rail 2200 of the present disclosure as illustrated in FIG. 26.

Figure 29:
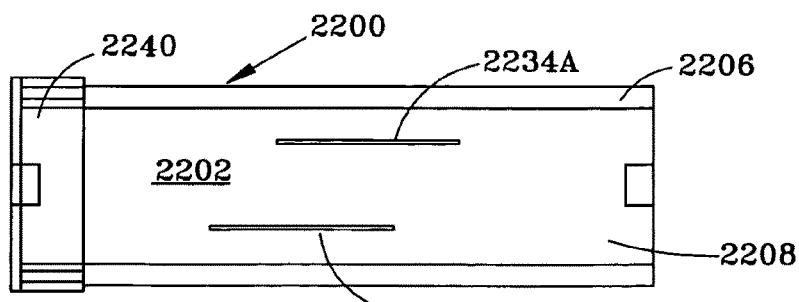
FIG. 29 is a plan view of the preferred embodiment of a ballast rail of the present disclosure as illustrated in FIG. 26 engaged with a collet.

FIG. 29 is a plan view of the preferred embodiment of the ballast rail 2200 of the present disclosure as illustrated in FIG. 26 engaged with a collet. The ballast rail 2200 comprises a planar portion 2202, an offset portion 2204, a lip portion 2206 and a beveled portion 2208. The planar portion 2202 has one or more ballast adjustment slots 2234A, 2234B for removeably securing a ballast to the ballast rail 2200. Also, a collet 2240 secures the ballast rail 2200 to the housing. The configurations illustrated in FIGS. 26, 27, 28, 29, 30 provide special and enhanced heat sink effects for the ballasts attached to the ballast rail 2200.

Figure 30:
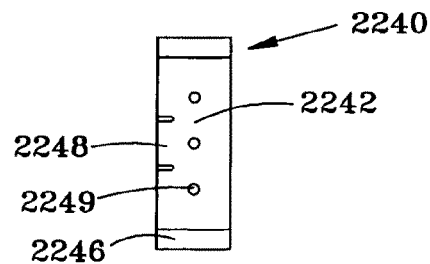
FIG. 30 is a plan view of the preferred embodiment of the collet of the present disclosure as illustrated in FIG. 29.

FIG. 30 is a plan view of the preferred embodiment of the collet 2240 of the present disclosure as illustrated in FIG. 29. The collet 2240 comprises a planar member 2242, a lip portion 2246, a beveled portion 2248 and one or more apertures 2249.

Figure 31:
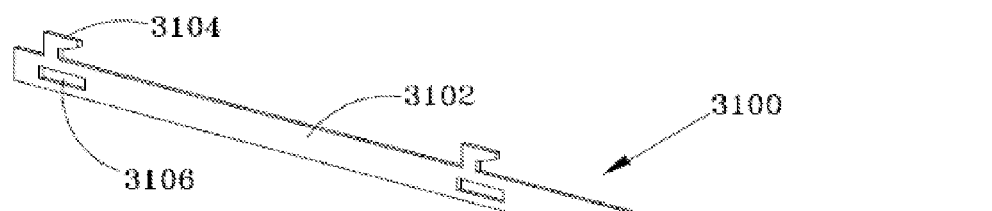
FIG. 31 is a perspective view of a preferred embodiment of a latch bar of the present disclosure.

FIG. 31 is a perspective view of a preferred embodiment of a latch bar 3100 of the present disclosure. The latch bar 3100 comprises a longitudinal member 3102, a latch 3104, an aperture 3106 and an angled portion 3108.

Figure 31A:
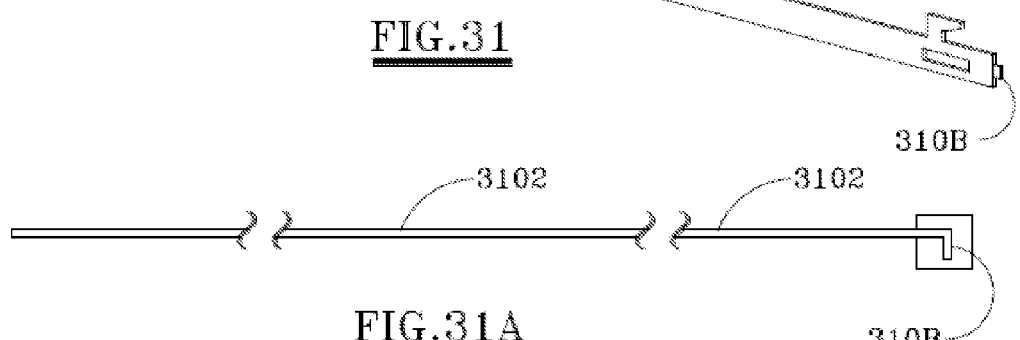
FIG. 31A is a longitudinal view of the preferred embodiment of the latch bar of the present disclosure as illustrated in FIG. 31.

FIG. 31A is a longitudinal view of the preferred embodiment of the latch bar 3100 of the present disclosure as illustrated in FIG. 31. The latch bar 3100 is illustrated with the angled portion 3108.

Figure 31C:
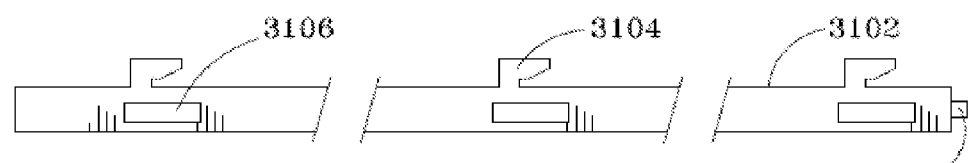
FIG. 31C is a longitudinal, break-away view of the preferred embodiment of the latch bar of the present disclosure as illustrated in FIG. 31.
Figures 31B, 31D:
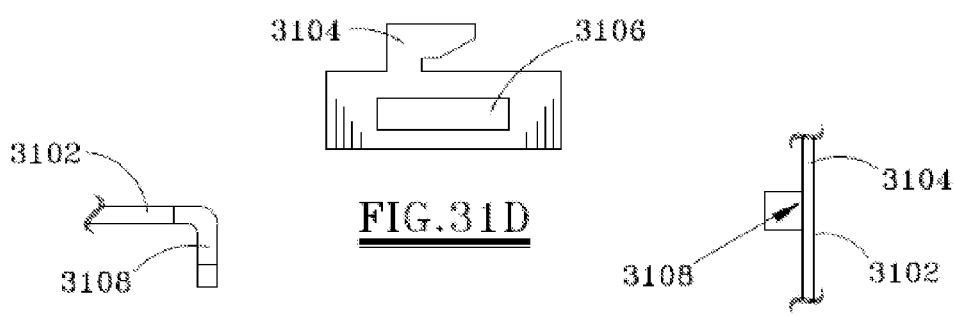
FIG. 31B is a detail view of the preferred embodiment of the latch bar of the present disclosure as illustrated in FIG. 31A.
FIG. 31D is a detail view of the preferred embodiment of the latch of the latch bar of the present disclosure as illustrated in FIG. 31A.
Figure 31E:
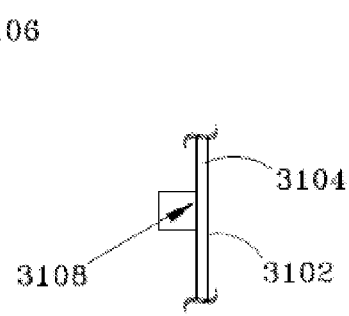
FIG. 31E is a detail view of the preferred embodiment of the latch bar of the present disclosure as illustrated in FIG. 31A.

FIG. 31B is a detail view of the preferred embodiment of the angled portion 3108 of the latch bar 3100 of the present disclosure as illustrated in FIG. 31A.

FIG. 31C is a longitudinal, break-away view of the preferred embodiment of the latch bar 3100 of the present disclosure as illustrated in FIG. 31. The latch bar 3100 is illustrated with the longitudinal member 3102, the latch 3104, the aperture 3106 and the angled portion 3108.

FIG. 31D is a detail view of the preferred embodiment of the latch of the latch bar 3100 of the present disclosure as illustrated in FIG. 31A. The latch bar 3100 is illustrated with the longitudinal member 3102, the latch 3104, the aperture 3106 and the angled portion 3108.

Figure 32A:
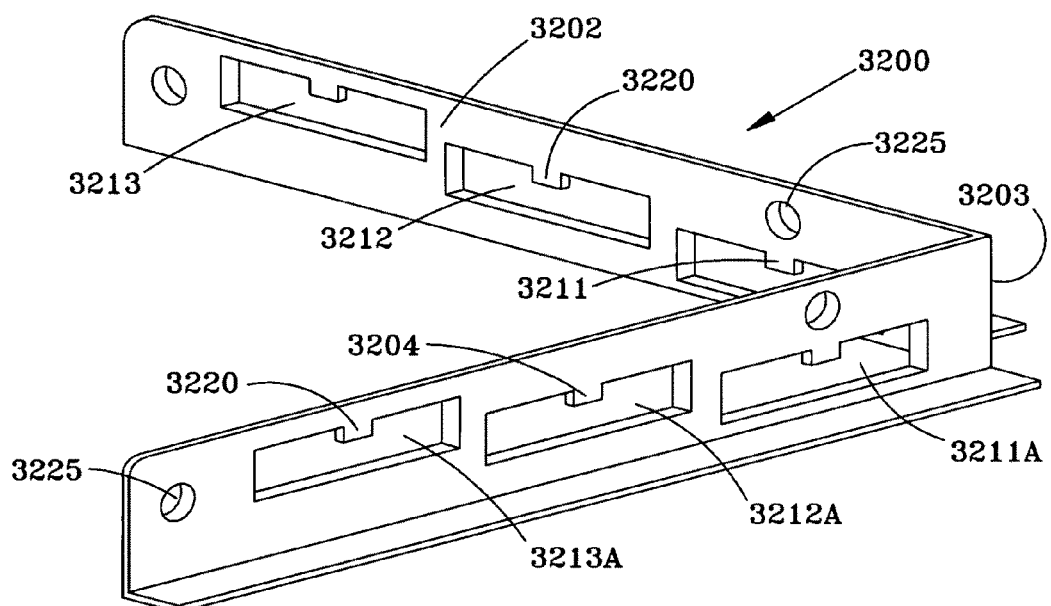
FIG. 32A is a perspective view of the preferred embodiment of the lens receiver guide of the present disclosure.

FIG. 32A is a perspective view of the preferred embodiment of the lens receiver guide 3200 of the present disclosure. The lens receiver guide 3200 comprises a first member 3202, a second member 3204, where the first member 3202 and the second member 3204 are separated by an angle 3203. The angle 3203 coincides with the angle at the corners of the lens cover, which in the present embodiment is 90 degrees. The first member 3202 and the second member 3204 have corresponding apertures 3211, 3111A, 3112, 3112A, 3113, 3113A. Each aperture 3211, 3111A, 3112, 3112A, 3113, 3113A has a protrusion 3220 therein. The protrusion 3220 is for removeably securing a lens clip 3300 (see FIG. 33) therein.

Figure 32B:
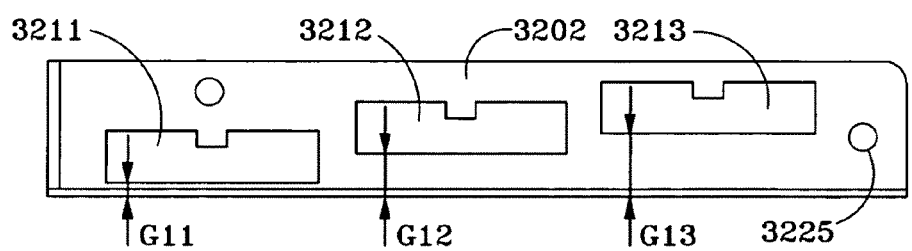
FIG. 32B is an elevation view of the preferred embodiment of the lens receiver guide of the present disclosure as illustrated in FIG. 32A.

FIG. 32B is an elevation view of the preferred embodiment of the lens receiver guide 3200 of the present disclosure as illustrated in FIG. 32A. The lens receiver guide 3200 has a first member 3202 with three apertures 3211, 3112, 3113. The number of apertures 3211, 3112, 3113 is determined by the number of thicknesses of lens that will be accommodated by the lens receiver guide 3200. In the embodiment illustrated, the three apertures 3211, 3112, 3113 correspond to lens with thicknesses of the three gaps, G11, G12 and G13.

Figure 32C:
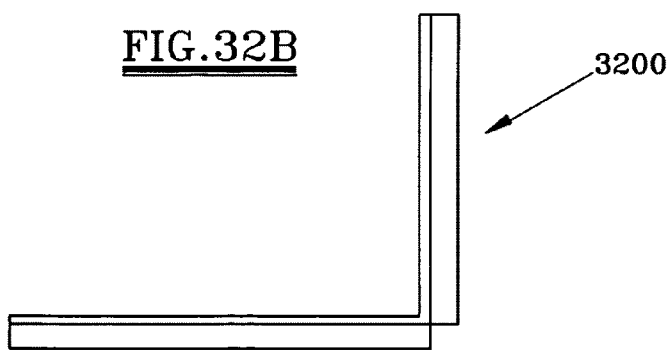
FIG. 32C is a plan view of the preferred embodiment of the lens receiver guide of the present disclosure as illustrated in FIG. 32A.

FIG. 32C is a plan view of the preferred embodiment of the lens receiver guide 3200 of the present disclosure as illustrated in FIG. 32A.

FIG. 33A is a perspective view of a preferred embodiment of the lens clip 3300 of the present disclosure. The lens clip 3300 comprises a base member 3302, a side member 3304, an angled member 3306, an engagement member 3308 and an pressing member 3310. The side member 3304 can be any shape, e.g., round or square. The angled member 3306 has an aperture 3312 therein. The aperture 3312 in the angled member 3306 of the lens clip 3300 is for receiving the protrusion 3220 in the aperture 3211 when the lens clip 3300 is engaged in the aperture 3211 of the lens receiver guide 3200. The lens clip 3300 is inserted for securing the lens and removed for changing the lens.

FIG. 33B is an elevation view of the preferred embodiment of the lens clip of the present disclosure as illustrated in FIG. 33A.

Modular Germicidal Insert

A modular germicidal insert 4000 is provided comprising an enclosure 4100 having a chamber 4200, an ultraviolet (UV) light source 4300, and an air mover 4400.

The modular germicidal insert 4000 is adapted to engage a light fixture 100. The chamber 4200 is adapted to provide mixing of the air passing through the chamber 4200. The UV light source 4300 is provided at such a wavelength as to destroy bacterial matter, such as by way of example, disrupting the DNA process within the bacterial matter. A sensing device 4500 can be used to test the processed air to determine the appropriate germicidal effectiveness. An automatic cut-off 4600 can be used to for power consumption. Thus, air is moved into the enclosure 4100, circulated within the chamber 4200, irradiated by the UV light source 4300, sensed by the sensing device 4500 to determine adequate germicidal effectiveness, and released to the area adjacent to the enclosure 4100.

FIG. 34 is a perspective view of an embodiment of a UV germicidal modular insert 4000 of the present disclosure.

FIG. 35 is a perspective view of another embodiment of a UV germicidal modular insert 4000 of the present disclosure.

Figure 36:
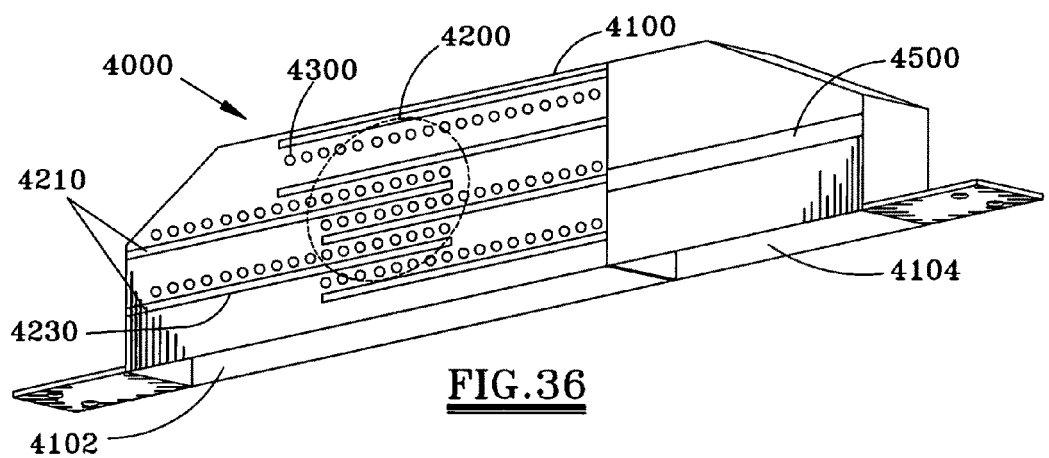
FIG. 36 is a cut-away view of a preferred embodiment of a UV germicidal modular insert of the present disclosure illustrating the chamber, a baffle, a UV light source, UV lamp sensing device, an inlet and an outlet.

FIG. 36 is a cut-away view of an embodiment of a UV germicidal modular insert 4000 of the present disclosure illustrating an enclosure 4100 having a chamber 4200, a baffle 4210, a UV light source 4300, a UV lamp sensing device 4500, with the enclosure 4100 having an inlet 4102 and an outlet 4104. A UV reflective material 4230 is attached to the surface of the baffle 4210 for enhancing the intensity of the germicidal UV radiation.

Figure 37:
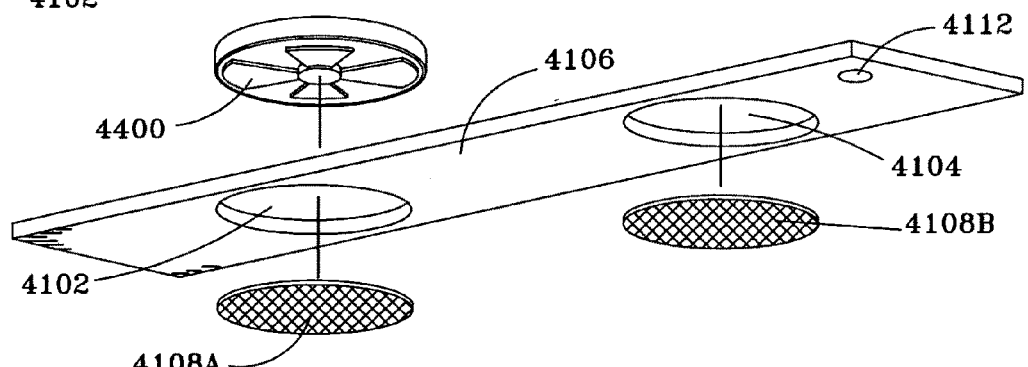
FIG. 37 is a cut-away view of a preferred embodiment of a UV germicidal modular insert of the present disclosure illustrating the chamber, a baffle, a UV light source, UV lamp sensing device, an inlet, an outlet, a fan, a cover plate, a fan grille, an exhaust outlet, an exhaust grille and an automatic cut switch for the power.

FIG. 37 is a cut-away view of a preferred embodiment of a UV germicidal modular insert 4000 of the present disclosure illustrating an enclosure 4100 having a chamber 4200, a baffle 4210, a UV light source 4300, UV lamp sensing device 4500, an inlet 4102, an outlet 4104, a fan or air mover 4400, a cover plate 4106, a fan grille 4108A, the exhaust outlet 4104, an exhaust grille 4108B and an automatic cut switch 4112 for the power.

Figure 38:
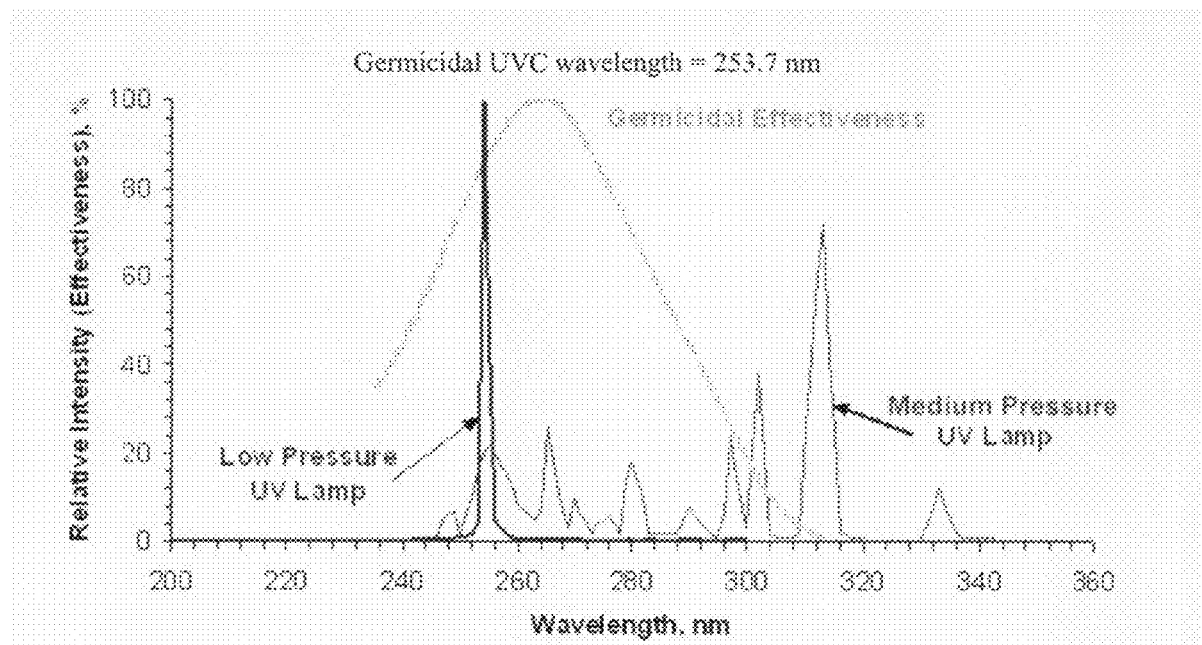
FIG. 38 is a graph of the relative intensity in percent verses the wavelength in nanometers illustrating the germicidal effectiveness.

FIG. 38 is a graph illustrating wavelength in nanometers versus percent germicidal effectiveness or relative intensity. UV radiation is artificially produced, typically, by mercury vapor, excimer and more recently LED lamps. The most effective lamps radiant energy in the germicidal wavelength of 253.7 nm, also known as the UVC part of the spectrum. As seen in FIG. 38, lamps have secondary emissions, including small amounts of UVA, UVB, visible light (above 400 nm wavelength) and heat. Reflective materials 4230 with high UVC reflection properties are used to multiply the UV efficiency of the UV germicidal lamps. ☐☐ There are various types of UVC lamps available for use with the present germicidal fixture and insert. Examples of lamps are: Cold Cathode Germicidal UV Lamps, Hot Cathode Germicidal UV Lamps, Slimline Germicidal Ultraviolet Lamps, High Output germicidal UV lamps, UV Light Emitting Diodes or UV LED lamps, as well as excimer UV lamps.

Figure 39:
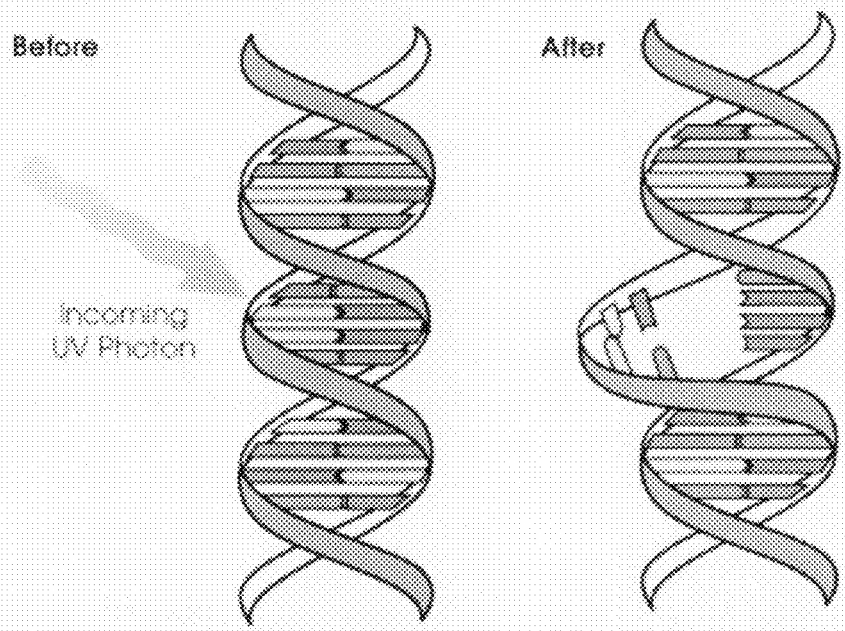
FIG. 39 is an illustration of the before and after effects of UV light on DNA related to germicidal matter.

FIG. 39 is a figure illustrating the eradication of germs using UV radiation. Germicidal ultraviolet (UVC) light kills cells by damaging their DNA. The light initiates a reaction between two molecules of thymine, one of the bases that make up DNA. UV light at this wavelength (shortwave UV or UVC) causes adjacent thymine molecules on DNA to dimerize. The resulting thymine dimer is very stable. If enough of these defects accumulate on a microorganism's DNA its replication is inhibited, thereby rendering it harmless. Further, UV photons harm the DNA molecules of living organisms in different ways. For example, adjacent bases bond with each other, instead of across the "ladder." This makes a bulge, and the distorted DNA molecule does not function properly. The longer the exposure to UVC light, the more thymine dimers are formed in the DNA. If cellular processes are disrupted because of DNA damage, the cell cannot carry out its normal functions. If the damage is extensive and widespread, the cell will die.

Many variables, such as for example, air flow, humidity, distance of microorganism to the UV light, and irradiation time, effect calculating the effective UV dosage. However, it is known in the art that UV light will kill any DNA-based microorganism given enough UV dosage. UV light breaks down DNA on a cumulative basis. Therefore, as air circulates through the chamber 4200 containing the UV light source 4300, the UV light continuously disinfects the air. If a microorganism is not effectively deactivated on the first pass through the chamber 4200, the UV light will continue to break the DNA down on subsequent passes. The UV germicidal fixture or insert requires microorganisms to be in a mobile, dynamic environment. Microorganisms multiply rapidly if not controlled. The UV germicidal fixture or insert helps to reduce airborne microorganisms from the indoor environment.

The present disclosure provides for varied designs of the UV germicidal fixture, adder box or attachment. Particularly, several general designs are available: the end-cap or adder box design, the ballast cover or attachment design, the internal design and the remote design.

Figure 40:
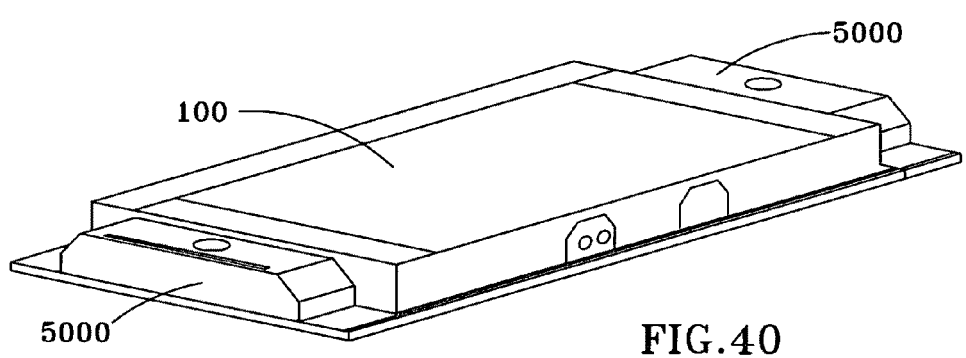
FIG. 40 is a perspective view of another preferred embodiment of a UV germicidal modular adder box of the present disclosure adapted for use with a fluorescent fixture.

FIG. 40 illustrates the end-cap or adder box design. FIG. 40 is a perspective view of another preferred embodiment of a UV germicidal modular adder box fixture 5000 of the present disclosure adapted for use with a fluorescent fixture 100. FIG. 40 illustrates an adder box germicidal fixture 5000. The adder box germicidal fixture 5000 is attached to the light fixture 100. The adder box germicidal fixture 5000 can be added onto either or both extremes of the light fixture 100. The adder box germicidal fixture 5000 is illustrated with the outer casing 5002.

Figure 41:
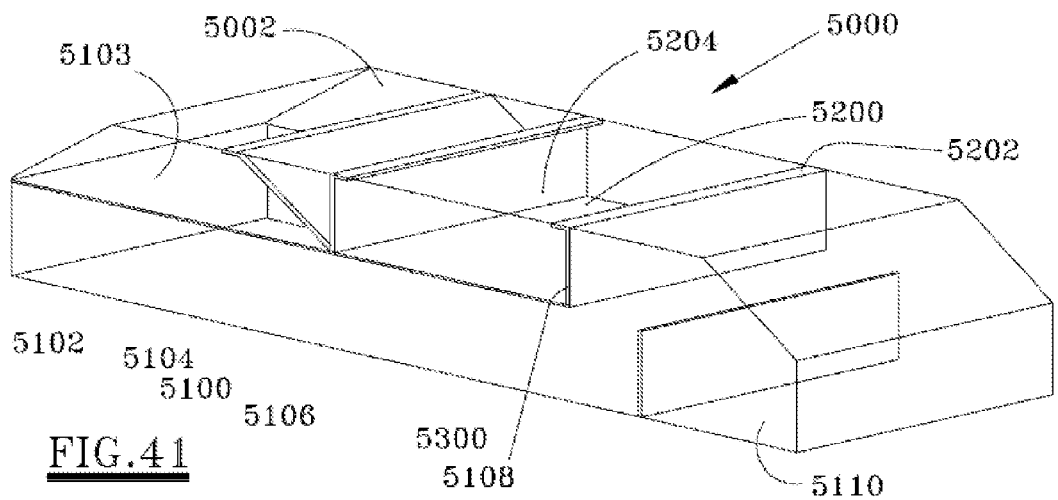
FIG. 41 is a perspective view of the preferred embodiment of a UV germicidal modular adder box of the present disclosure as illustrated in FIG. 40.

FIG. 41 is a perspective view of the preferred embodiment of a UV germicidal modular adder box germicidal fixture 5000 of the present disclosure as illustrated in FIG. 40. FIG. 41 is a perspective view of the adder box germicidal fixture 5000 illustrating the flow assembly 5100 and the light assembly 5200. The flow assembly 5100 includes an air mover 5102, an entrance chamber 5103, a baffle 5104, an irradiation chamber 5106, a second baffle 5108 and an exit chamber 5110. The flow assembly 5100 provides for the air mover or fan 5102 to bring into the adder box fixture 5000 a specific flow rate of air. The air mover 5102 provides that the airflow comes into the entrance chamber 5103 and is deflected by the baffle 5104. The baffled air enters the irradiation chamber 5106 in a turbulent state. The baffled air has a sufficiently high Reynolds number of above 4000 so that turbulent flow is maintained. Although not required, a turbulent state having a Reynolds number above 4000 provides for enhanced effectiveness of the irradiated matter. Further, the size of the irradiation chamber 5106 is provided to be proportional to the residence time of the specific germicidal matter being irradiated. Thus, for example, if the time to irradiate a specific germicidal matter for the destruction of that matter requires a longer residence time then the size of the chamber can be modified. Similarly, the flow rate of the air mover 5102 can be altered to increase or decrease the air flow, as well. Variables of importance are, without limitation, the residence time, the flow rate, the UV intensity and the state of turbulence.

The baffles 5104, 5108 provide that the UV light within the irradiation chamber 5106 is contained within the chamber. A sensor 5300 is provided for multiple purposes. First, the sensor 5300 is provided for measuring the intensity of the UV light within the irradiation chamber 5106. If the light goes out or is not within a specific intensity, a signal indicates maintenance is needed for the germicidal fixture 5000. Also, the sensor 5300 can be used to test the germicidal matter within the irradiation chamber 5106 to provide an indication of the degradation achieved while the germicidal matter is within the irradiation chamber 5106. The airflow is again baffled by the second baffle 5108. The the second baffle 5108 is also a source of turbulence within the irradiation chamber 5106. The airflow passes around the second baffle 5108 and into the exit chamber 5110. The light assembly 5200 comprises the mounts 5202 and the UV lamps 5204. It can be appreciated by those skilled in the art that any light assembly adaptable for use with UV lamps would be useable in the present disclosure.

Figure 42:
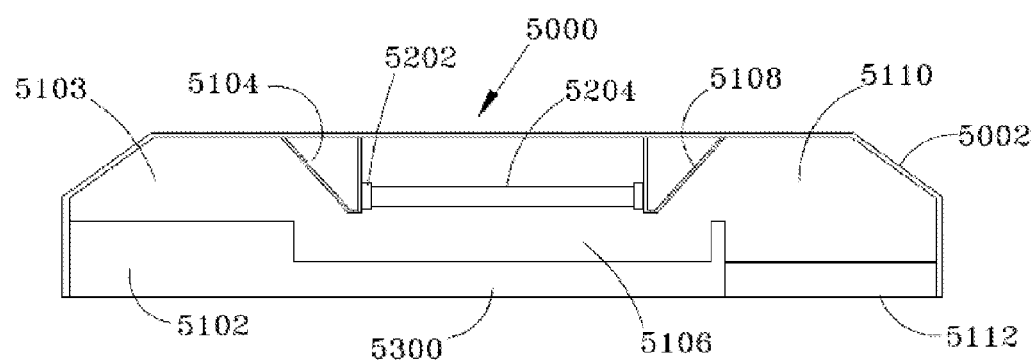
FIG. 42 is an elevation view of the preferred embodiment of a UV germicidal modular adder box of the present disclosure as illustrated in FIGS. 40 and 41.

FIG. 42 is an elevation view of the preferred embodiment of a UV germicidal modular adder box of the present disclosure as illustrated in FIGS. 40 and 41. FIG. 42 is an elevation, cutaway view of the adder box germicidal fixture 5000 illustrated in FIG. 41. The air mover or fan 5102 is provided for the ingress of air bearing germicidal matter into the entrance chamber 5103. The entrance chamber 5103 provides turbulence which is enhanced by the baffle 5104 prior to the germicidal matter entering the irradiation chamber 5106. In the irradiation chamber 5106, the germicidal matter is contained for a sufficient residence time so as to achieve the desired degradation of the germicidal matter for achieving the desired disinfection of the germicidal matter. The disinfected germicidal matter passes from the irradiation chamber 5106 around the baffle 5108, and into the exit chamber 5110. The treated germicidal matter exits the chamber 5110 via an exit port 5112. The mounts 5202 are illustrated supporting the UV lamps 5204. The casing 5002 provides that the flow assembly 5100 and the light assembly 5200 are enclosed.

Figure 43:
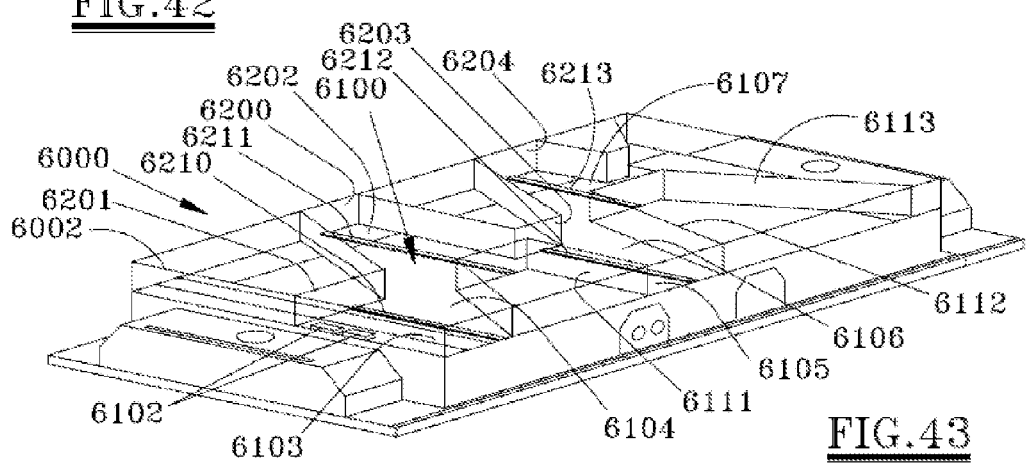
FIG. 43 is a perspective view of another preferred embodiment of a UV germicidal modular attachment of the present disclosure adapted for use with a fluorescent fixture.

FIG. 43 illustrates the ballast cover or attachment design. FIG. 43 is a perspective, cut-away view of another preferred embodiment of a UV germicidal modular attachment of the present disclosure adapted for use with a fluorescent fixture.

Figure 44:
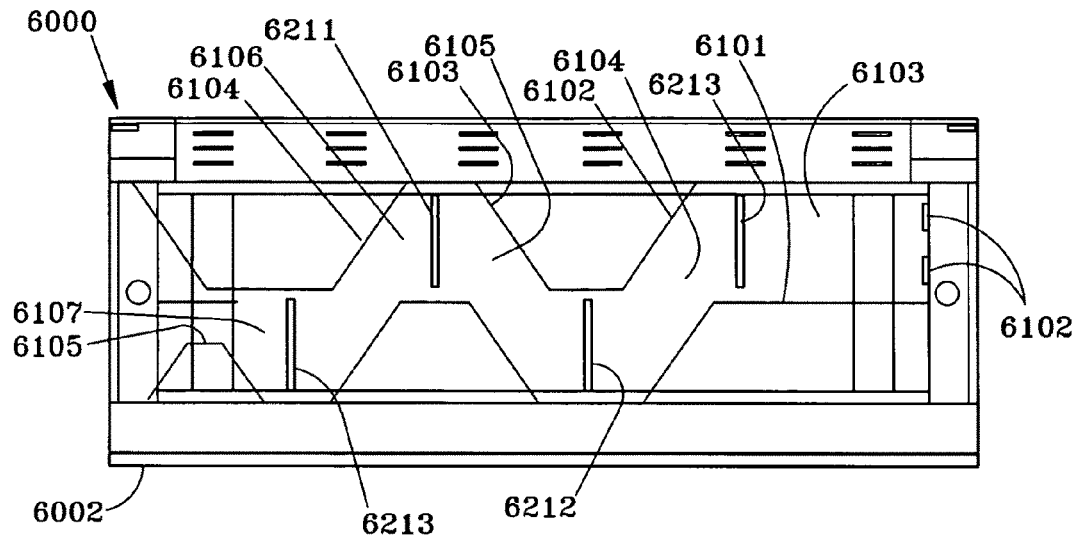
FIG. 44 is a top, cut-away view of the preferred embodiment of the UV germicidal modular attachment of the present disclosure as illustrated in FIG. 43.

FIG. 44 is a top, cut-away view of the preferred embodiment of the , UV germicidal modular attachment of the present disclosure as illustrated in FIG. 43. FIG. 44 illustrates a perspective, cut-away view of the attachment UV germicidal fixture 6000 of the present disclosure. The attachment germicidal fixture 6000 comprises a flow assembly 6100 and a light assembly 6200. The flow assembly 6100 comprises a first irradiation chamber 6103, a first baffle 6101, a second irradiation chamber 6104, a second baffle 6102, a third irradiation chamber 6105, a third baffle 6103, a fourth irradiation chamber 6106, a fourth baffle 6104, a fifth irradiation chamber 6107 and a fifth baffle 6105. The light assembly 6200 comprises a first UV irradiator 6210, a second UV irradiator 6211, a third UV irradiator 6212 and a fourth UV irradiator 6213. The respective irradiators are provided with supports and UV light emitters. Also, the attachment germicidal fixture 6000 comprises the air mover 6102, which is illustrated as two fans. Further, the attached germicidal fixture 6000 has a case 6002 for enclosing the flow assembly 6100 and the light assembly 6200.

Figure 45:
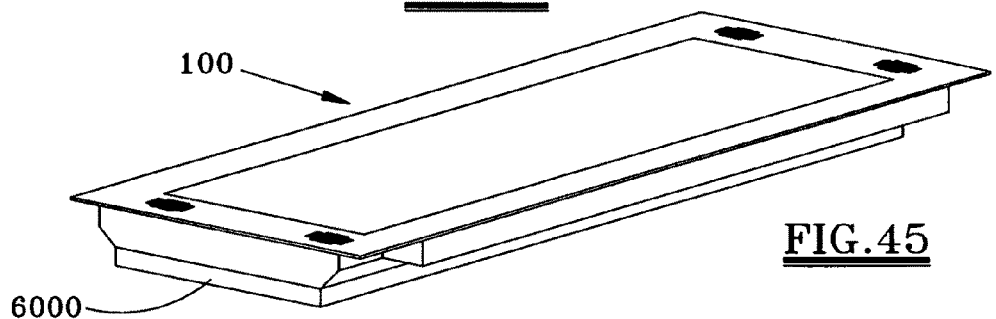
FIG. 45 is a perspective view of the UV germicidal modular attachment of the present disclosure as illustrated in FIGS. 43 and 44.

FIG. 45 is a perspective view of the UV germicidal modular attachment of the present disclosure as illustrated in FIGS. 43 and 44. FIG. 45 illustrates a fixture 100 associated with an attachment germicidal fixture 6000 and an adder box germicidal fixture 5000.

Figure 46:
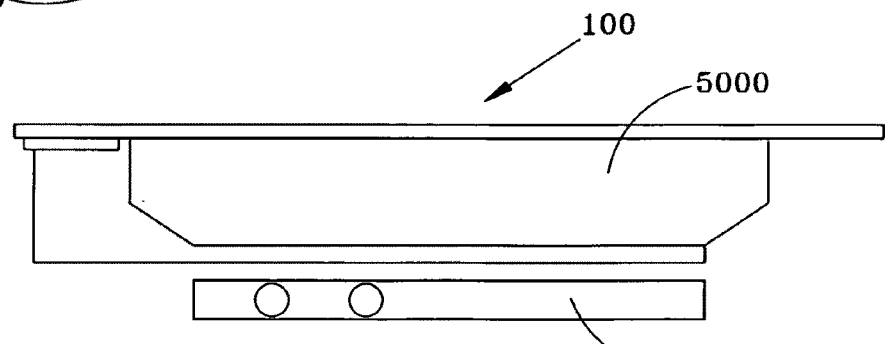
FIG. 46 is an end view of the UV germicidal modular attachment of the present disclosure as illustrated in FIGS. 43, 44 and 45.

FIG. 46 is an end view of the UV germicidal modular attachment of the present disclosure as illustrated in FIGS. 43, 44 and 45. FIG. 46 is an end view with an adder box germicidal fixture 5000 and an attachment germicidal fixture 6000 in association with a fixture 100.

Additional advantages and modification will readily occur to those skilled in the art. The disclosure in its broader aspects is therefore not limited to the specific details, representative apparatus, and the illustrative examples shown and described herein. Accordingly, the departures may be made from the details without departing from the spirit or scope of the disclosed general inventive concept.

The invention claimed is:

1. A germicidal light kit comprising
an enclosure, a flow assembly and a UV light assembly, the germicidal light kit for engagement with a light fixture engaged with a ceiling, the ceiling comprising an essentially planar surface,
the light fixture comprising
   a housing comprising a concaved inner surface and a convexed outer surface, the concaved inner surface defining an aperture with a perimeter having a plurality of sides that forms a cavity,
   a cover trim member for engagement with the housing for enclosing the cavity when the cover trim member is engaged with the perimeter of the concaved surface of the housing and for extending longitudinally beyond the two extremities of the housing to form a projection the projection having at least one aperture therein,
   a ballast rail having minimal engagement with the convexed outer surface of the housing for receiving a ballast and positioning the ballast remote from the housing and exterior of the cavity formed by the housing such that the ballast and the ballast rail are in engagement with the surrounding environment, such that the light fixture is affixed to the ceiling in a pivotal relationship having a first position with the light fixture in the same planar surface as the ceiling during operation of the light fixture and a second position with the light fixture pivoted from one of the sides of the perimeter at an approximately 90° displacement from the ceiling with the ballast exterior of the housing cavity and in an open accessible location for easy repair, removal, maintenance, installation or a combination thereof, the enclosure of the germicidal light kit is engaged with the projection of the cover trim adjacent to the ballast rail such that the air is taken in and exhausted through the apertures of the cover trim.

2. The germicidal light kit of claim 1 wherein the flow assembly comprises an air mover, an entrance chamber, at least one baffle, an irradiation chamber and an exit chamber for moving air through the flow assembly.

3. The germicidal light kit of claim 2 wherein the airflow in the irradiation chamber is turbulent.

4. The germicidal light kit of claim 2 wherein the turbulent airflow in the irradiation chamber has a Reynolds number of above 4000.

5. The germicidal light kit of claim 1 further comprising a sensor for measuring the intensity of the UV light within the irradiation chamber, and, if appropriate, signaling for maintenance, for testing the germicidal matter within the irradiation chamber to provide an indication of the degradation achieved while the germicidal matter is within the irradiation chamber, or a combination thereof.

6. The germicidal light kit of claim 2 wherein the flow assembly is coated with reflecting, microbial, impregnated, "clean" surfaces or a combination thereof.

7. A germicidal light fixture comprising
an enclosure,
a flow assembly comprising an air mover, an entrance chamber, at least one baffle, an irradiation chamber and an exit chamber for moving air through the flow assembly,
a UV light assembly in operative association with the irradiation chamber, and
a sensor for measuring intensity of the UV light within the irradiation chamber, and generating a signal for maintenance corresponding to the intensity
wherein the germicidal light fixture is configured for engagement with a pre-existing light fixture.

8. The germicidal light fixture of claim 7 wherein the airflow in the irradiation chamber is turbulent.

9. The germicidal light fixture of claim 8 wherein the turbulent airflow in the irradiation chamber has a Reynolds number of above 4000.

10. The germicidal light fixture of claim 7 wherein the sensor or an additional sensor test the germicidal matter within the irradiation chamber to provide an indication of the degradation achieved while the germicidal matter is within the irradiation chamber.

11. The germicidal light fixture of claim 7 wherein said at least one baffle is coated with reflecting, microbial, impregnated, "clean" surfaces or a combination thereof.

12. A germicidal light kit comprising an enclosure, a flow assembly and a UV light assembly, wherein the enclosure is configured to engage a portion of a pre-existing light fixture.

* * * * *